United States Patent [19]
Johnston et al.

[11] Patent Number: 5,815,278
[45] Date of Patent: Sep. 29, 1998

[54] SURFACE PLASMON RESONANCE LIGHT PIPE SENSING PROBE AND RELATED INTERFACE OPTICS

[75] Inventors: Kyle Johnston, Bothell; Sinclair S. Yee, Seattle, both of Wash.

[73] Assignee: University of Washington, Seattle, Wash.

[21] Appl. No.: 738,442

[22] Filed: Oct. 25, 1996

Related U.S. Application Data

[60] Provisional application No. 60/007,027 Oct. 25, 1995, provisional application No. 60/005,878 Oct. 26, 1995 and provisional application No. 60/009,169 Dec. 22, 1995.

[51] Int. Cl.[6] .............................. G01N 21/00; G02B 6/02
[52] U.S. Cl. .............................................. 356/445; 385/12
[58] Field of Search ................................... 356/128, 445; 385/12

[56] References Cited

U.S. PATENT DOCUMENTS

| | | | |
|---|---|---|---|
| 4,844,613 | 7/1989 | Batchelder et al. | 356/318 |
| 4,889,427 | 12/1989 | Van Veen et al. | 356/445 |
| 4,997,278 | 3/1991 | Finlan et al. | 356/128 |
| 5,055,265 | 10/1991 | Finlan | 422/82.05 |
| 5,064,619 | 11/1991 | Finlan | 422/82.05 |
| 5,120,131 | 6/1992 | Lukosz | 356/351 |
| 5,313,264 | 5/1994 | Ivarsson et al. | 356/73 |
| 5,327,225 | 7/1994 | Bender et al. | 356/445 |
| 5,351,127 | 9/1994 | King et al. | 356/445 |
| 5,359,681 | 10/1994 | Jorgenson et al. | 385/12 |
| 5,374,563 | 12/1994 | Maule | 436/165 |
| 5,425,124 | 6/1995 | McRight et al. | 385/123 |
| 5,474,815 | 12/1995 | Sunderland | 427/576 |
| 5,478,755 | 12/1995 | Attridge et al. | 436/518 |
| 5,485,277 | 1/1996 | Foster | 356/445 |
| 5,492,840 | 2/1996 | Malmqvist et al. | 436/518 |

FOREIGN PATENT DOCUMENTS

| | | |
|---|---|---|
| 2 174 802 | 11/1986 | United Kingdom . |
| 2 186 387 | 8/1987 | United Kingdom . |
| WO 88/08992 | 11/1988 | WIPO . |
| WO 89/07756 | 8/1989 | WIPO . |

OTHER PUBLICATIONS

Bussjager, R. and Macloud, H. (1995), "The inverted surface plasmon resonance: further discussion," *J. Modern Optics* 42(7):1355–1360.

Gordon, J.G and Ernst, S. (1980), "Surface Plasmons as a Probe of the Electrochemical Interface," *Surf. Sci.* 101:499–506.

Ishimaru, A. *Electromagnetic Wave Propagation, Radiation, and Scattering,* Prentice Hall, Englewood Cliffs, NJ (1991) Chapter 3 pp. 43–45.

Johnston, K.S. et al (1995), "New analytical technique for characterization of thin films using surface plasmon resonance," *Mater. Chem. Phys.* 42:242–246.

Jorgenson, R.C. and Yee, S.S. (1993) "A Fiber Optic Chemical Sensor Based on Surface Plasmon Resonance," *Sensors and Actuators B* 12:213–220.

Jorgenson, R.C. and Yee, S.S. (1994) "Control of the Dynamic Range and Sensitivity of a Surface Plasmon Resonance Based Fiber Optic Sensor" *Sensors and Actuators A* 43:44–48.

(List continued on next page.)

*Primary Examiner*—Richard A. Rosenberger
*Attorney, Agent, or Firm*—Greenlee, Winner & Sullivan, P.C.

[57] ABSTRACT

The present invention provides SPR sensors in which the sensing element is a planar lightpipe. The sensors of this invention include configurations that employ multi-wavelength light (including broad band and white light) incident on the SPR sensing area at a single angle or at a range of angles. Sensors and probes of this invention also include configurations that employ monochromatic light at a range of angles. Many of the configurations of the SPR lightpipes of this invention involve imaging of input light through the folded lightpipe. In one general embodiment, the invention provides a SPR sensor system in which the sensing element is a folded planar lightpipe.

46 Claims, 18 Drawing Sheets

OTHER PUBLICATIONS

Jory, M.J. et al. (1994), "Development of a prototype gas sensor using surface plasmon resonance on gratings," *Sensors and Actuators B* 17:203–209.

Jung, C. (1991), "Surface Plasmon Resonance," Master Thesis, University of Washington.

Jung, C. et al. (1995), "Electro–optic polymer light modulator based on surface plasmon resonance," *Appl. Opt.* 34(6):946–949.

Jung, C.C. et al. (1995) "Fiber–Optic Surface Plasmon Dispersive Index Sensor for Highly Opaque Samples" *Process Control and Quality* 7:167–171.

Karlsen, S.R. et al. (1995), "Simultaneous Determination of Refractive Index and Absorbance Spectra of Chemical Samples Using Surface Plasmon Resonance," *Sensors and Actuators B* 24–25:747–749.

Kretschmann, E. and Raether, H. (1968) "Radiative Decay of Non–radiative Surface Plasmons Excited by Light" *Z. Naturforsch., Teil A,* 23:2135–2136.

Kreuwel, H.J.M. et al. (1987) "Surface Plasmon Dispesion and Luminescence Quenching Applied to Planar Waveguide Sensors for the Measurement of Chemical Concentrations," *Proc. SPIE* 798:218–224.

Lambeck, P.V. (1992) "Integrated Opto–Chemical Sensors" *Sensors and Actuators B* 8:103–116.

Lavers, C.R. and Wilkinson, J.S. (1994), "A waveguide–coupled surface–plasmon sensor for an aqueous environment," *Sensors and Actuators B* 22:75–81.

Liedberg, B. et al. (1983), "Surface plasmon resonance for gas detection and biosensing," presented at Solid–State Transducers 83, Delft, The Netherlands, Ma7y 31–Jun. 3, 1983, pp. 299–304.

Mar, M. et al. (1993 ) "In–Situ Characterization of Multi-layered Langmuir–Blodgett Films Using a Surface Plasmon Resonance Fiber Optic Sensor" Proc. of the 15th Annual Conf. of the IEEE Engineering in Medicine and Biology Soc., San Diego, CA pp. 1551–1552.

Nelson, S.G. et al. (1996) "High Sensitivity Surface Plasmon Resonance Sensor Based on Phase Detection" presented at the Sixth International Conference on Chemical Sensors (Jul. 22–24, 1996) Washington, D.C.

Pockrand, I. et al. (1979) "Exciton–Surface Plasmon Interactions" *J. Chem. Phys.* 70:3401–3408.

Printz, M. et al. (1993), "An inverted surface plasmon resonance," *J. Modern Optics* 40(11):2095–2104.

Ruiz, E. Garcia et al. (1993), "Industrial process sensor based on surface plasmon resonance (SPR) 1. Distillation process monitoring," *Sensors and Actuators A* 37–38:221–225.

Smith, W.J. (1992), *Modern Optical Engineering, The Design of Optical Systems,* 2nd ed. (McGraw Hill), pp. 192–195, 263–265.

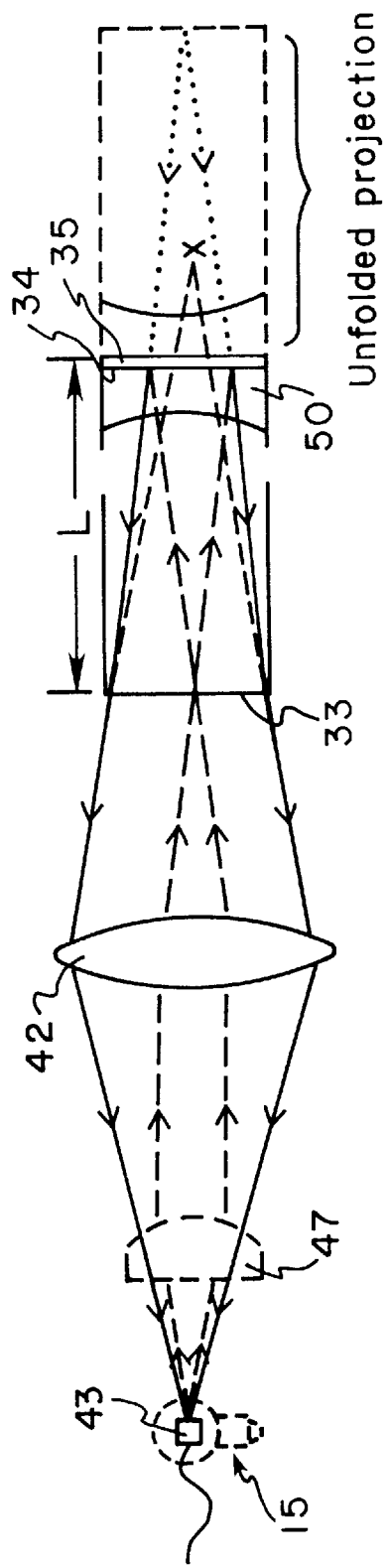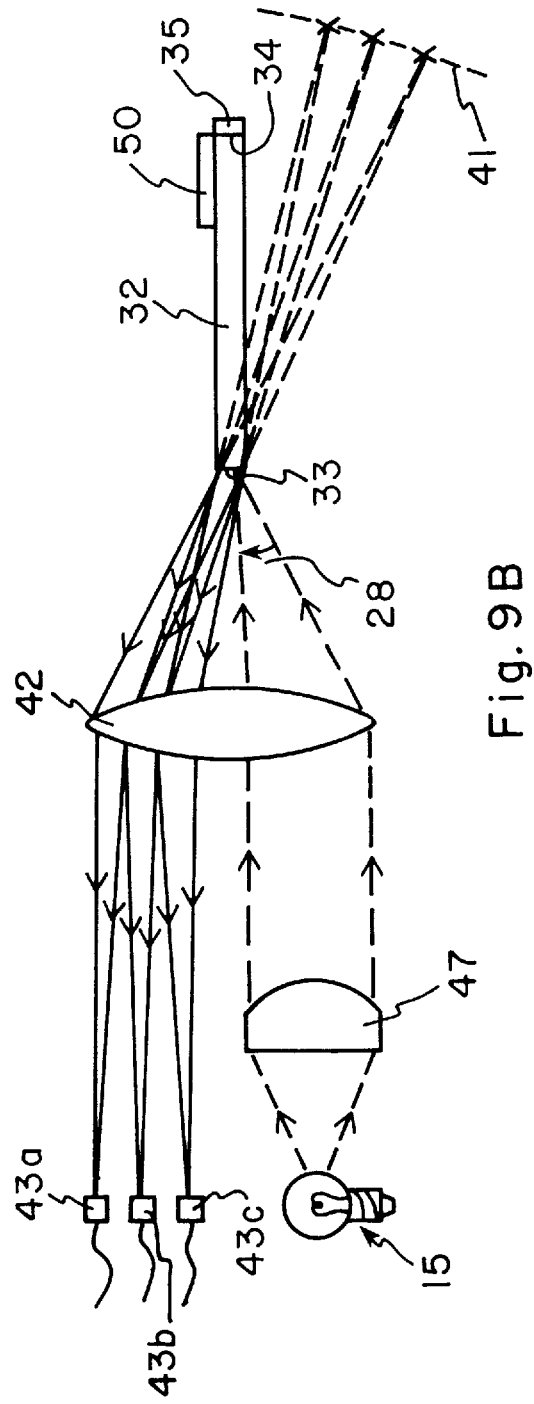
Fig. 9A
Fig. 9B

SURFACE PLASMON RESONANCE LIGHT PIPE SENSING PROBE AND RELATED INTERFACE OPTICS

This invention was made, at least in part, with support from the National Science Foundation under grant number EID-9212314. The United States Government has certain rights in this invention.

CROSS-REFERENCE TO RELATED APPLICATIONS

This application claims the benefit of priority under 35 U.S.C. 119(e) of U.S. provisional patent applications Ser. Nos. 60/007,027 filed Oct. 25, 1995; 60/005,878 filed Oct. 26, 1995; and 60/009,169 filed Dec. 22, 1995, each of which are incorporated in their entirety by reference herein.

FIELD OF THE INVENTION

This invention relates in general to surface plasmon resonance sensors and more particularly to sensors employing a folded planar lightpipe sensor configuration. Configurations of these sensors can be employed for either or both wavelength modulation or angular modulation SPR.

BACKGROUND OF THE INVENTION

Optical surface plasmon resonance (SPR) sensors are sensitive to changes in the refractive index (RI) of a sample near the sensor surface. Most bulk prism SPR sensor configurations measure either the angular reflection spectrum for monochromatic light or the wavelength reflection spectrum for collimated white light.

SPR sensors have become popular laboratory tools for applications such as the monitoring of immuno-assays and enzyme reactions. In addition to biochemical sensing, SPR sensors have also been shown to function as high resolution refractometers. There is potential for utilizing these sensing abilities in industrial process control applications such as environmental waste stream monitoring, pharmaceutical production, and food/beverage preparation. However, SPR sensors have apparently not been successfully applied in commercial process control applications.

For use in commercial process control, a sensor must be compatible with the operating conditions of the desired application and have a low failure rate. Additional necessary sensor characteristics include: real time measurements; compatibility with on-line or in-situ sensing; long term stability of sensor readings; repeatable sensor response; robust sensor components and mechanism; inexpensive sensing elements that can be reused or that are sufficiently inexpensive and simple to make so that they can be considered disposable; and sensor response that can be accurately calibrated.

A goal of the present work has been to develop a versatile, stable and inexpensive SPR sensor that can satisfy the requirements of industrial process control, yet retain sensitivity comparable to bulk optic SPR configurations which will make the sensor useful for biosensing applications. SPR sensor configurations with moving parts (e.g., angle scanning tables) will not be sufficiently stable and reliable. SPR systems designed as laboratory bench-top units will not be sufficiently low cost and are not compatible with on-line or in-line sensing . Finally, waveguide or fiber optic SPR configurations that rely on single point intensity measurements will not be sufficiently stable or reproducible and will be difficult to calibrate.

The fiber optic SPR probe developed by Jorgenson and Yee U.S. Pat. No. 5,359,681 is a low cost, disposable fiber optic sensor that can operate as an immersible dip probe and has sensitivity comparable to bulk optic SPR configurations. Despite the utility and simplicity of its design, this fiber optic SPR probe has several drawbacks resulting from its cylindrical sensing substrate. The fiber optic sensor requires the use of nonstandard deposition equipment to fabricate the SPR sensing layer on the fiber. Thus, it is difficult to ensure that a stable, uniform sensing layer has been created. Certain types of fibers, for example those with easy-to-strip cladding, may not be compatible with temperatures needed to stabilize the sensing film via annealing. There also may be difficulty in maintaining the angular distribution of the light propagating in a flexible fiber, causing variations in calibration and potential nonrepeatability of measurements.

This invention provides a new SPR probe with a planar lightpipe sensing element that can be constructed from inexpensive materials, for example standard microscope slides. The sensing element comprises an optically folded lightpipe in which the SPR sensing area and the input and output optics of the sensor can be readily separated allowing for convenient probe configurations. These configurations maintain the advantages of the fiber optic SPR probe such as low cost and compatibility with in-situ and on-site sensing, while eliminating most of the difficulties discussed above in the construction and testing of the sensors. Additionally, the probe simultaneously measures on several independent channels, making it the first SPR probe capable of both multiplexing and first order sensing.

Various SPR sensor configurations utilizing waveguides, including optical fibers, have been reported. These include a single-mode planar waveguiding structure which detects intensity changes in monochromatic light (Lavers, C. R. and Wilkinson, J. S. (1994) "A Waveguide-Coupled Surface-Plasmon Sensor for an Aqueous Environment" *Sensors and Actuators B* 22:75–81) and a sensor system in which white light is injected into a single-mode waveguide having an SPR supporting superstructure (Kreuwel, H. J. M. et al. (1987) "Surface Plasmon Dispersion and Luminescence Quenching Applied to Planar Waveguide Sensors for the Measurement of Chemical Concentrations," *Proc. SPIE* 798:218–224; Lambeck, P. V. (1992) "Integrated Opto-Chemical Sensors" *Sensors and Actuators B* 8:103–116). Additionally, a white light multi-mode fiber optic SPR sensor has been introduced (U.S. Pat. No. 5,359,681, issued October 1994); Jorgenson, R. C. and Yee, S. S. (1993) "A Fiber Optic Chemical Sensor Based on Surface Plasmon Resonance," *Sensors and Actuators B* 12:213; Jung, C. C. et al. (1995) "Fiber-Optic Surface Plasmon Dispersive Index Sensor for Highly Opaque Samples" *Process Control and Quality* 7:167–171; Jorgenson, R. C. and Yee, S.S. (1994) "Control of the Dynamic Range and Sensitivity of a Surface Plasmon Resonance Based Fiber Optic Sensor" *Sensors and Actuators A* 43:44–48; Mar, M. et al. (1993) "In-Situ Characterization of Multilayered Langmuir-Blodgett Films Using a Surface Plasmon Resonance Fiber Optic Sensor" Proc. of the 15th Annual Conf. of the IEEE Engineering in Medicine and Biology Soc., San Diego, Calif. pp. 1551–1552.

U.S. Pat. No. 5,485,277 (filed Jul. 26, 1994, issued Jan. 16, 1996) "Surface Plasmon Resnance Sensor and Methods for the Utilization Thereof " reports an SPR sensor said to comprise a "waveguide" cartridge, a cylindrical diverging lens coupled to the "waveguide" and a plurality of photodetectors optically connected to the cylindrical lens. The "waveguide", exemplified by a microscope slide with angled input and output faces, carries a symmetrically positioned metal layer that supports SPR. Apparently, monochromatic light is introduced into the "waveguide" through the angled polished input face by focusing the light through the end of the "waveguide" onto the metal sensor surface at a range of angles spanning the angular location of the surface plasmon resonance. The RI of the sample is determined by measuring light intensity exiting the sensor as a function of angle. The patent also discusses the use of sensing and reference channels on the same metal film-coated waveguide.

SPR folded lightpipe sensors of this invention can be employed as first order sensors. SPR sensor waveguide configurations that have been reported are limited to those measuring refractive index at either a single wavelength or a single angle (angular or wavelength modulation, respectively). Such configurations are considered zero order sensors since they measure only one independent variable for a given analyte. Recently, a first order SPR sensor geometry that can simultaneously measure a sample's index of refraction at multiple wavelengths was reported (Karlsen, S. R. et al. (1995), "Simultaneous Determination of Refractive Index and Absorbance Spectra of Chemical Samples Using Surface Plasmon Resonance," *Sensors and Actuators B* 24–25:747–749). This dispersive RI sensor which employed a cylindrical sapphire prism with a gold sensing layer required several discrete optical components which introduced optical aberrations in the reflected signal, making it difficult to calibrate both the angular and spectral outputs of the sensor.

Thus, there remains a need in the art for SPR sensors that are versatile, stable, inexpensive, retain high sensitivity and which can be designed to function as probes in in-situ or on-line sensing applications or in other process control application. In addition, there remains a need for first order SPR sensors that allow independent measurements of two variables for a given analyte providing dispersive RI information and for SPR sensors allowing the simultaneous determination of two parameters, for example, film thickness and RI of a thin film applied to an SPR sensing surface. There is also a need in the art, particularly for assay of biological samples, for SPR sensors that can simultaneously detect more than one analyte in a sample (multiplexed sensors). There also generally remains a need for SPR sensors which are sensitive, simple to use, readily calibrated, compact in size and rugged, and inexpensive to produce. SPR sensors of this invention meet these needs.

SUMMARY OF THE INVENTION

The present invention provides SPR sensors in which the sensing element is a planar lightpipe. The sensors of this invention include configurations that employ multiwavelength light (including broad band and white light) incident on the SPR sensing area at a single angle or at a range of angles. Sensors and probes of this invention also include configurations that employ monochromatic light at a range of angles. Many of the configurations of the SPR lightpipes of this invention involve imaging of input light through the folded lightpipe.

In one general embodiment, the invention provides a SPR sensor system in which the sensing element is a folded planar lightpipe. An optically folded lightpipe is fabricated from a transparent or semi-transparent material. It has a top and bottom planar surface and two longitudinal ends. A mirror is deposited on one longitudinal end of the lightpipe, the distal end, to fold the optical path of the lightpipe. Light is launched into the other longitudinal end of the lightpipe, is conducted down the lightpipe by total internal reflection (TIR), and reflects off the mirrored distal end of the lightpipe to ultimate exit the lightpipe at the end by which it entered the lightpipe, designated the input/output end.

The folded lightpipe comprises an SPR sensing area on one or both of its external planar surfaces. Light coupled into the lightpipe reflects off the back side of one or more SPR sensing areas of the lightpipe before exiting the lightpipe. Light exiting the lightpipe comprises SPR features. The sensing areas on the external surfaces of the lightpipe comprise an SPR-supporting conducting layer, preferably an SPR-supporting metal layer. The sensing area can in principle be positioned anywhere on either or both of the planar surfaces of the lightpipe. The sensing area is preferably positioned on the planar surface at the distal end of the lightpipe extending at most 75% of the length of the folded lightpipe toward the input/output end. In a more preferred configuration, the sensing area (s) is positioned on a planar surface to start at the distal end of the lightpipe extending up to about ⅔ (up to about 66%) of the length of the lightpipe toward the input/output end.

Folded lightpipe SPR sensors also comprise a light source, a multiwavelength light source being preferred. The light source is optically coupled to the input/output end of the folded lightpipe such that input light is conducted through the lightpipe by TIR, to reflect off the mirror and exit the lightpipe through the input/output end. If input light comprises a range of angles, light will exit the lightpipe in discrete angular bands. Each angular band is the spectral output of a small range of incidence angles. Combined spectral analysis of individual angular bands provides dispersive RI of a given sample or analyte.

Folded lightpipe SPR sensors also comprise a detector for surface plasmon resonance which can receive and analyze the spectral content (intensity as a function of wavelength) of angular bands of light exiting the lightpipe that have been reflected off an SPR sensing area.

Light that is coupled into the lightpipe input face at a range of angles propagates through the lightpipe by total internal reflection (TIR), making multiple reflections, and exits in a series of angular bands each containing spectral information (including SPR features) for a small range of incidence angles. A detector or detectors are positioned to measure the reflection spectrum, including any surface plasmon resonance feature, of one or preferably more than one of the angular bands exiting the lightpipe. The same sensor configuration can be employed to measure SPR from a range of incidence angles of monochromatic input light (simple angular modulation)or to measure SPR from a range of incidence angles of more than one wavelength. The measurement of a broad range of angles and wavelengths allows the measurement of a dispersive RI curve (i.e., RI as a function of wavelength) of a given sample or analyte.

Light can be coupled into and out of the lightpipe sensors of this invention in a variety of ways using conventional optical apparatus to focus, collimate and/or selectively expand light on coupling into the lightpipe or to focus, collimate, disperse, and/or collect light exiting the lightpipe. Incident light must comprise TM polarized light. The light employed in the sensor is optionally TM polarized to remove the TE component prior to launch into the sensor. Alternatively, the TE component light of light is removed by passage through a TM polarizer any time prior to detection.

Preferred embodiments of the folded lightpipe sensors of this invention employ telecentric lens systems for simultaneously focusing light into the folded lightpipe and collecting and redirecting angular output bands into a detector. Telecentric lens employed in these configurations include cylindrical and spherical telecentric lenses.

The folded planar lightpipe of the sensors of this invention has at least one SPR sensing area on at least one of its planar surfaces. A SPR sensing area comprises an SPR-supporting conducting layer, preferably an SPR-supporting metal layer and optionally has an adherence layer, dynamic range-controlling layers and reactive layers. In particular embodiments, the SPR sensors of this invention can have a plurality of sensing areas along the length or both of a lightpipe surface or across the width of the lightpipe or both. Lightpipes of the sensors of this invention can include both active and reference sensing areas and active sensing areas on a given lightpipe can have sensing areas specific for the same or different analytes in a sample.

SPR sensors of this invention can include static or flow sample cells to confine samples for SPR measurements. A preferred embodiment of a SPR probe of this invention is a dip probe that can be inserted into a given sample to detect one or more analytes in the sample. This invention includes multichannel and multiplexed SPR sensors having a plurality of independent SPR sensing areas on a planar lightpipe surface. In addition, sample cells can be configured to contact different sensing areas on the lightpipe surface with different samples.

Lightpipes of the sensors of this invention can be fabricated from a variety of materials transparent or semi-transparent to the input light. Glass, crystal, including sapphire, as well as plastic and polymer materials can be used for lightpipe substrate. Lightpipes optionally have a cladding layer to insure TIR of light along the length of the lightpipe.

SPR Lightpipe sensors of this invention can be employed as biosensors, particularly to detect multiple analytes in biological samples, such as serum or blood. SPR lightpipe sensors of this invention can also be employed as refractometers to monitor the RI of a sample.

The folded lightpipe SPR sensors of this invention are compatible with all SPR sensing applications previously identified for both the benchtop planar SPR sensors and the fiber optic SPR sensor probe. In addition, they have many attributes that improve sensor performance and open up new applications. These folded lightpipe configurations have a simplified sensor construction compatible with standard processing techniques, employ lower cost disposable sensor substrates that can also be reused, have easily controllable dynamic sensing range by choice of substrate material and signal band that is monitored, have improved sensitivity because of sharper resonant signals, allow simple multiplexing on a single sensor, are compatible with existing fiber optic SPR sensing instrumentation and compatible with hand-held SPR systems in development. Since each band of signal light produces an independent measurement, these configurations are first order SPR sensors and probes that are capable of measuring more than one characteristic of a given analyte at a time. These sensors also have automatic angular calibration, minimal optical aberrations, and do not require index matching fluids. In one embodiment, a folded lightpipe sensor can be fabricated from inexpensive, disposable microscope slide providing an SPR probe which can measure dispersive RI of a sample in a simple, compact, and inexpensive manner.

Light can be coupled into and out of the lightpipe sensors of this invention in a variety of ways using conventional optical apparatus and components to focus, collimate and/or selectively expand light on coupling into the lightpipe or to focus, collimate, disperse, and/or collect light exiting the lightpipe.

This invention provides SPR sensors with optically folded planar lightpipe sensing elements and method of detecting analytes in samples using these sensors. The invention also provides folded planar lightpipe that have a plurality of SPR sensing layers on a planar surface.

BRIEF DESCRIPTION OF THE FIGURES

FIGS. 7A and 7B are not necessarily drawn to scale.

FIG. 9A is a top view and FIG. 9B a side view not necessarily drawn to scale of an alternative folded lightpipe configuration of this invention. The sensing area on the top surface of the lightpipe is curved along its width (at the side of the sensing area toward the input-output end of the lightpipe) to minimize multiple reflections off the sensing surface.

FIG. 11A is a top view and FIG. 11B is a side view.

DETAILED DESCRIPTION OF THE INVENTION

A surface plasmon wave is an electromagnetic wave which propagates along the interface between a conductor (or semi-conductor) and a dielectric, and decays normal to the interface. A plasmon is the collective oscillations of free charges, ions or valence electrons, in a metal or semiconductor which can be excited by a polarizing interaction (a polaritron) between an electromagnetic wave and an oscillator resonant at the same frequency as the wave. A surface plasmon polaritron is the interaction between photons and the collective oscillations of electrons at the surface of a conductor. The interaction is strongest at the resonance condition known as surface plasmon resonance, which is satisfied when the tangential component of the wave vector of light incident on the conductor is equal to the wave vector of the surface plasmon wave. Incident light satisfying the resonance condition causes surface charges on the conductor to oscillate creating a bound electromagnetic or charge-density wave propagating along the interface between the conductor and a dielectric material. The resonance condition depends on the wavelength of incident light and the angle at which light is incident upon the interface as well as the dielectric constants of all of the materials in the layers involved, including that of a dielectric sample in contact with the sensing layer.

For the case in which a metal SPR-supporting layer on a supporting dielectric substrate (e.g., glass) is in contact with a dielectric sample, the resonance condition is:

$$k_x = k_o n_{substrate} \sin(\theta_{inc}) = k_{sp}, \quad (1)$$

where $k_o = 2\pi/\lambda$ is the free space wave vector of the incident light, $\theta_{inc}$ is the incident angle of the light, $n_{substrate}$ is the complex, wavelength-dependent refractive index (RI) of the substrate. The wave vector of surface plasmon wave, $k_{sp}$, can be approximated as (Jung, C. (1991), "Surface Plasmon Resonance," Master Thesis, University of Washington)

$$k_{sp} \approx k_0 \left[ \frac{\epsilon_d \epsilon_m}{\epsilon_d + \epsilon_m} \right]^{\frac{1}{2}} \quad (2)$$

where $\epsilon_d$ and $\epsilon_m$ are the wavelength dependent complex dielectric permitivities of the dielectric sample and metal. The wavelength dependent permittivity is related to the refractive index by the equation:

$$\epsilon = \epsilon(\lambda) = n(\lambda)^2 = (n' - jn'')^2 \quad (3)$$

Figure 1A:
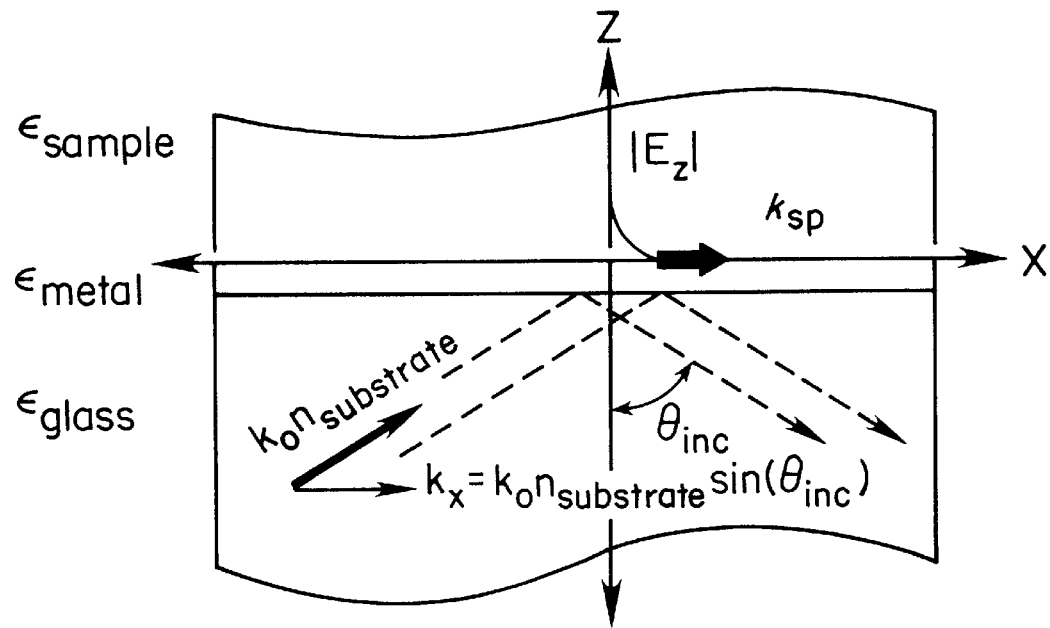
FIG. 1A is a schematic drawing of wave vector matching on an SPR sensor with a three layer structure.

Most generally an SPR sensor uses a three layer structure as illustrated in FIG. 1A, in which light is incident on the back side of a thin metal (or other conductor) sensing film at an angle of incidence $\theta_{inc}$ which is greater than the critical angle for total internal reflectance ($\theta_{critical}$). One implication of Equation 2 is that SPR cannot be excited directly on a two-layer smooth interface because $k_x$ will always be smaller than $k_{sp}$ regardless of the values of $\theta_{inc}$. However, Equation 2 can be satisfied for a three-layer interface if $n_{glass} > n_{sample}$, $\theta_{inc} > \theta_{critical}$ and a highly conductive metal, an SPR-supporting metal such as silver or gold, is used. Another implication of Equation 2 is that SPR cannot be excited with TE polarized light, for which $k_x = 0$.

Two experimental methods are commonly used to monitor the excitation of SPR. "Angle modulation" utilizes the Kretschmann configuration in which a range of angles of monochromatic light are incident onto the back side of the metal sensing layer which is brought into contact with a solid, liquid or gas dielectric sample creating a metal-dielectric interface that will support SPR. (Kretschlnann, E. and Raether, H. (1968) "Radiative Decay of Non-radiative Surface Plasmons Excited by Light" Z. Naturforsch., Teil A, 23: 2135–2136). In "wavelength modulation," the incident light is collimated but has a range of wavelength. TM-polarized collimated white light is incident upon the back side of a sensing surface at a single angle and intensity of the light reflected from that surface is measured as a function of wavelength, for example, using a spectrograph. As stated above, resonance depends upon both the wavelength of incident light and the angle or angles at which the light hits the sensing interface (incidence angle(s)).

Figure 1B:
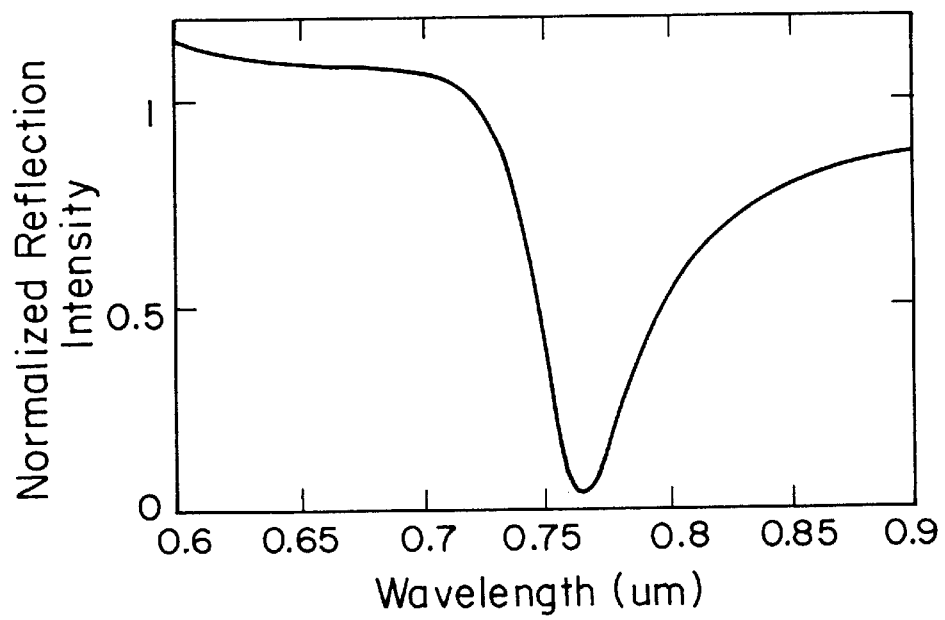
FIG. 1B is a simulated reflection spectrum from a white light SPR sensor showing attenuation (as a function of wavelength) due to SPR.

For both of these methods, the incident light contains a range of wave vectors, and the reflection spectrum is attenuated around the wave vector that best matches the value of $k_{sp}$. The excitation of SPR is most often detected experimentally as a decrease in the reflection coefficient (i.e., a decrease in intensity) of TM polarized light reflected off the sensing interface. This is illustrated for a white light SPR sensor in FIG. 1B. The attenuation feature is centered around the wavelength of maximum attenuation ($\lambda_{SPR}$). The actual shape of the reflection spectrum curve in FIG. 1B cannot be predicted using Equations 1 and 2, but must be modeled numerically using Fresnel reflection coefficients. See: Ishioaru, A. *Electromagnetic Wave Propagation, Radiation, and Scattering*, Prentice Hall, Englewood Cliffs, N.J. (1991) Chapter 3 pp. 43–45.

These traditional zero order sensing techniques hold one variable (angle or wavelength) constant and measure the reflection coefficient as a function of the other variable. For angle modulated SPR at a fixed wavelength, there can be an angle $\theta_{SPR}$ that satisfies the resonance condition. For a fixed angle, there can be a wavelength $\lambda_{SPR}$ at which the wavelength dependent permitivities (or RI's) of the various media are such as to satisfy the resonance condition. The angle or wavelength at which resonance (i.e., minimum reflected light intensity) is observed gives a measure of the effective index of refraction (RI) of the dielectric sample. The resonant angle ($\theta_{spr}$) or wavelength ($\lambda_{spr}$) can be calibrated (using samples of known concentration) to the refractive index of the sample.

Surface plasmon resonance sensors using only wavelength or angle modulation are considered zero order sensors because the vector of reflected intensities I($\theta$) or I($\lambda$)) is reduced to a single value of ($\theta_{spr}$) or ($\lambda_{spr}$). The previously reported bulk optic first order SPR sensor (Karlsen, S. R. et al. (1995), "Simultaneous determination of refractive index and absorbance spectra of chemical samples using surface plasmon resonance," *Sensors and Actuators B* 24–25:747–749) simultaneously monitored reflection coefficients over a range of angles and a range of wavelengths. This approach produces a matrix of data which can be reduced to a vector of RI values at different wavelengths.

The SPR excitation condition is extremely sensitive to the changes in the refractive index of the dielectric layers (e.g., substrate and sample) surrounding the SPR-supporting conductor sensing layer. The refractive index of a dielectric sample (in a sensor with a given substrate) can be detected by monitoring the SPR condition. Any shift in resonance curves ($\delta\theta_{spr}$ or $\delta\lambda_{spr}$) indicates a change in refractive index at the conductor/sample interface. In biochemical sensing, a shift results from a change in the effective RI ($n_{effective}$) experienced by the SPW due to the introduction of bulky molecules onto the sensor surface. With appropriate engineering, SPR sensors are capable of resolving less than $1\times10^{-5}$ refractive index units (IRU) or layers of biochemical molecules that average less than 1 $\mu$m thick.

SPR measures the complex refractive index of the sample in contact with the sensing area of the lightpipe. This complex refractive index includes both the real and imaginary refractive index components. The real component is inversely proportional to the speed at which light propagates through the sample, and is generally considered the "true" refractive index of the sample. The imaginary component is related to the sample's absorbance or attenuation of light. SPR sensors can thus be used to measure the absorbance of a sample as well as its index of refraction.

The SPR sensors of this invention employ a planar lightpipe configuration. As used herein the term lightpipe relates to a three dimensional structure that confines optical energy and allows it to be conducted from one point to another point with minimal loss by total internal reflection (TIR). The dimensions of a lightpipe are large in comparison to the wavelength of light to be confined and conducted therein, so that a lightpipe allows a continuous range of directions of light propagation within its boundaries. In addition, due to its relatively large dimensions the propagation of light within a lightpipe can be modeled using ray theory rather than mode theory. In contrast to a lightpipe, a waveguide is a three dimensional structure that confines and conducts light having dimensions comparable to the wavelength of light it confines and conducts. Light in a waveguide retains modal properties; it may be single-mode or multi-mode, but the allowed wave vector values are not continuous as in a lightpipe. The propagation of light in a waveguide, except when there are a very large number of modes, i.e., when the waveguide is almost a lightpipe, can be modeled using mode theory, but not ray theory.

Figure 2:
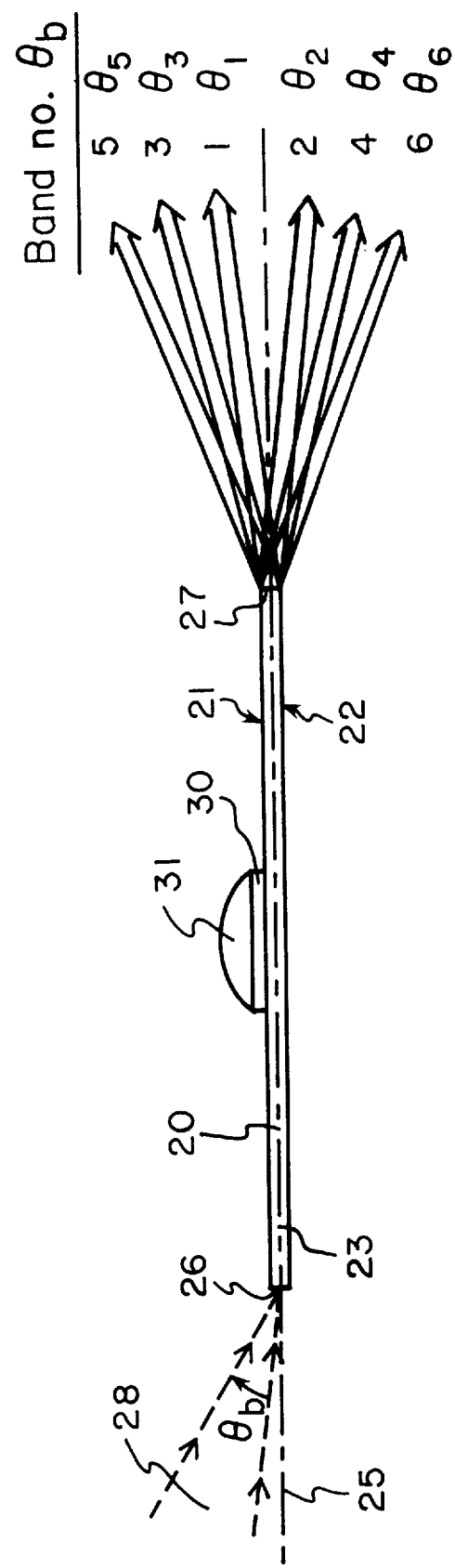
FIG. 2 is a schematic drawing not necessarily drawn to scale of a lightpipe SPR sensor in which input light is end-coupled into the lightpipe at a range of angles above the axis of the lightpipe. Light exits the output end of the lightpipe in an angular array of bands alternating above and below the axis.

A first order SPR planar lightpipe sensor configuration is illustrated in the side view of FIG. 2. In this configuration, input light is coupled into the lightpipe at one end (input) and exits at the other end (output). These in-line or transmission SPR lightpipe sensors are the subject of U.S. provisional applications Ser. No. 60/007,027 filed Oct. 25, 1995 and 60/005,878 filed Oct. 26, 1995 as well as the corresponding regular U.S. patent application (Attorney Docket No. 89-95) filed on Oct. 25, 1996.

Figure 7A:
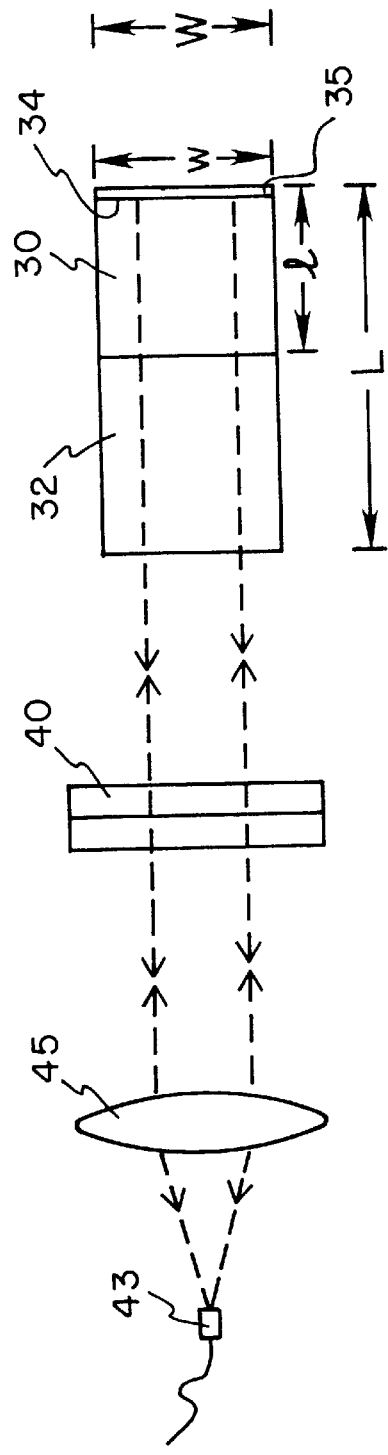
FIG. 7A is a top view of a folded lightpipe configuration of this invention having a telecentric lens in the input/output optics of the lightpipe.

The sensor of FIG. 2 comprises a planar lightpipe (20) having top (21) and bottom (22) planar surfaces, sides (23) and input (26) and output (27) end faces. A lightpipe is fabricated from a dielectric substrate material that is substantially transparent to input light. For example, various types of glass and crystals, including sapphire, and various types of plastics and polymers can be employed as the lightpipe materials. The planar lightpipe can be a uniform slab of substrate with uniform length (L), width (W) and thickness(t), where the length is defined as the dimension along which light traverses the lightpipe. The longitudinal input and output ends of the lightpipe can be beveled. In the configuration illustrated light is end-coupled into and out of the lightpipe in which the input and output ends are polished at about 90° to be substantially perpendicular to the planar top and bottom surfaces of the lightpipe. The SPR sensing area (30) of the illustrated sensor is fabricated on one planar surface of the lightpipe, which is designated as the top surface in all configurations described herein. The sensing area having length (l) and width(w), as indicated in FIG. 7A, is illustrated in FIG. 2, as placed centrally on the lightpipe surface. A sample cell (31) allows the sensing area to interface with a dielectric sample. Collimated white light (28), from a light source (not shown) is asymmetrically coupled into the input end of the lightpipe, for example by focusing the light, through a cylindrical lens (not shown) at the input face at a continuous range of angles ($\theta_b$) filling angles on only the upper side of the optical axis (25) of the lightpipe.

When the planar lightpipe is asymmetrically illuminated, as illustrated in FIG. 2, the output consists of discrete angular bands (b) (e.g., b=1–6 in FIG. 2) (Smith, W. J. (1992), *Modern Optical Engineering, The Design of Optical Systems*, 2nd ed., (McGraw Hill), p. 192). As the propagation angle ($\theta_b$) increases down from the axis (corresponding to increasing band numbers in FIG. 2), the direction of the output alternates in bands above or below the lightpipe axis. This is caused by the alternating number of reflections inside the lightpipe, with an odd number of reflections causing the rays to be directed down, and with an even number, directed up. Each discrete angular output band contains a different white light SPR reflection spectrum that represents the average over a small range of angles, which is approximately equal to t/L radians.

In practice, the fact that these bands are diverging and do not come from a common source requires some care to capture and measure several bands simultaneously. The folded lightpipe configurations herein provide a method for dealing with the diverging bands which has also allowed us to design an SPR probe based on a light pipe. In these folded configurations, the light enters and exits from the same face (the input/output face) of the sensor, the folded sensor designs can be utilized as probes that are dipped into the sample under test.

Figure 3:
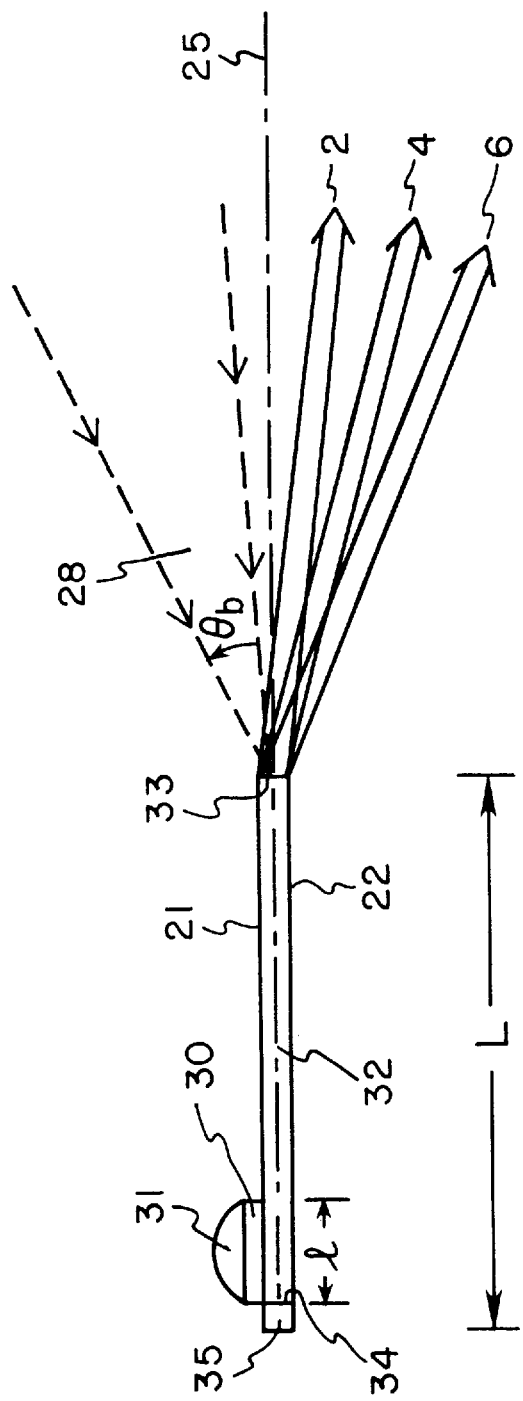
FIG. 3 is a schematic drawing not necessarily drawn to scale of a folded lightpipe sensor of this invention in which input light is end-coupled into the lightpipe at a range of angles above the axis of the lightpipe. Light exits the output end of the lightpipe in an angular array of bands alternating above and below the axis.

FIG. 3 illustrates the basic folded lightpipe geometry of this invention. In this figure, lightpipe 32 has two planar surface, a top surface (21) and a bottom planar surface (22), above and below the optic axis (25) in this figure, and two ends, an input/output end (33) and a distal end (34) which is mirrored (35). The distal end of the lightpipe is polished perpendicularly (or at a desired angle) and a mirror is deposited, or a mirror can be simply glued to the distal end. A sensing area 30 is positioned on the lightpipe near the distal end of the lightpipe. The sensor is provided with a sample cell 31. Light is input into the lightpipe at a range of angles ($\theta_b$,28) and exits the lightpipe in discrete angular bands as shown for the straight-through lightpipe of FIG. 2.

In the figures describing these configurations the surface carry the sensing area in the figure is called the top surface. All figures are illustrated with sensing areas on only one surface. However, sensing areas can be placed on both surfaces. In addition, all of the illustrated configurations employ asymmetric light input even though symmetric light input would also function for all illustrated configurations. Asymmetric light input above or below the lightpipe axis is defined as "above" or "below" with respect to the surface that has the sensing area in the figures herein.

By utilizing a mirror at one end of the sensing element, as shown in FIG. 3, the result is a "folded" SPR lightpipe sensor configuration which is the optical equivalent of the unfolded lightpipe sensor.

In both the lightpipes of FIGS. 2 and 3, the range of angles in each band is determined by the ratio of the length over the thickness of the sensor substrate. The higher the ratio, the smaller the range of angles subtended by each band and the sharper the resonant feature in the signal spectrum. However, a high dimension ratio means the average propagation angle of adjacent bands are closer together, which can cause physical difficulties in separating and capturing the signal light. Regardless of the thickness of the substrate, each band of light reflects off the top surface in a pattern of locations that are different from band to band. The pattern is determined only by the band number and the length of the substrate. The metallic sensing film must be carefully located such that all the bands of interest encounter the sensing film and end up with an attenuated SPR signal in their reflection spectrum.

In order to optimize the geometry of a lightpipe sensor and optimize the location of sensors on the lightpipe for a particular application, it is necessary to know the angular range of each band and the locations at which the band reflects off of the top surface (where the sensing layer will be positioned.) The angular extremes of each band can be calculated by "unfolding" the lightpipe multiple times as described in Smith, W. J. (1992), *Modern Optical Engineering, The Design of Optical Systems*, 2nd ed., (McGraw Hill), p. 192. Unfolding of the lightpipe, the calculation of locations for band reflections on the planar lightpipe surfaces and the optimization of sensing area position on the external lightpipe surface are described in detail in U.S. patent application Ser. No. 08/738,360 filed Oct. 25, 1996 which is based on a U.S. provisional application Ser. No. 60/007,027 filed Oct. 25, 1995.

Figure 4:
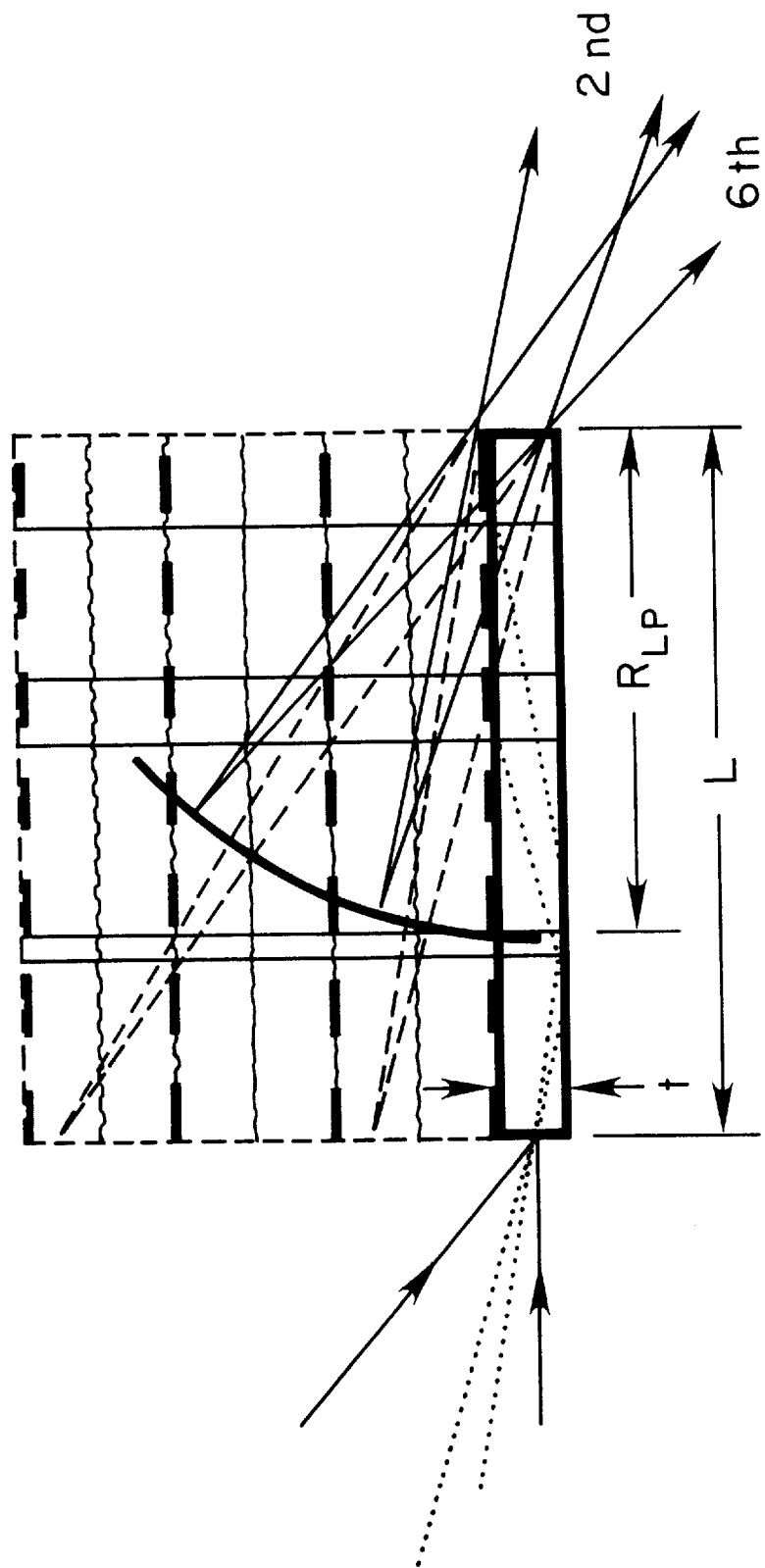
FIG. 4 is a drawing of an unfolded lightpipe showing trace rays for bands 2 and 6 where the band name indicates the number of internal reflections. The shaded locations show where band 6 interacts with the top surface of the sensor. Refraction at the output face causes the bands to appear as if they originate at point sources along an arc with radius $R_{LP}$.

Unfolding the light pipe as shown in FIG. 4 allows the ray paths through the light pipe to be analyzed. When this is done, the light rays appear to straighten out, as shown in FIG. 4, and it can be seen that the different bands hit different locations along the length of the top surface, and that the extreme rays for each band are defined by the lines from the source spot to the top and bottom of the aperture formed by the virtual lightpipe end.

Assuming a point source at the input, each output band occupies a unique range of angles which is determined by the length (L) and thickness (t) of the lightpipe. Additionally, there are specific locations where each band reflects off the top surface of the lightpipe which are unique and not shared with any other band. Therefore, if different samples are placed to coincide with the different band reflection locations, the lightpipe makes a naturally multiplexed SPR sensor with a different signal on each band. If the whole sensor is exposed to the same sample, the lightpipe produces multiple independent measurements, resulting in a first order sensor that can simultaneously determine more than one characteristic of the sample.

The bands of light refract when they leave the output face of the light pipe. This causes them to appear as if they were coming from discrete points along a virtual arc with a radius $R_{LP}$ where:

$$R_{LP} = \frac{L}{n_{substrate}} \quad (3)$$

Figure 5A:
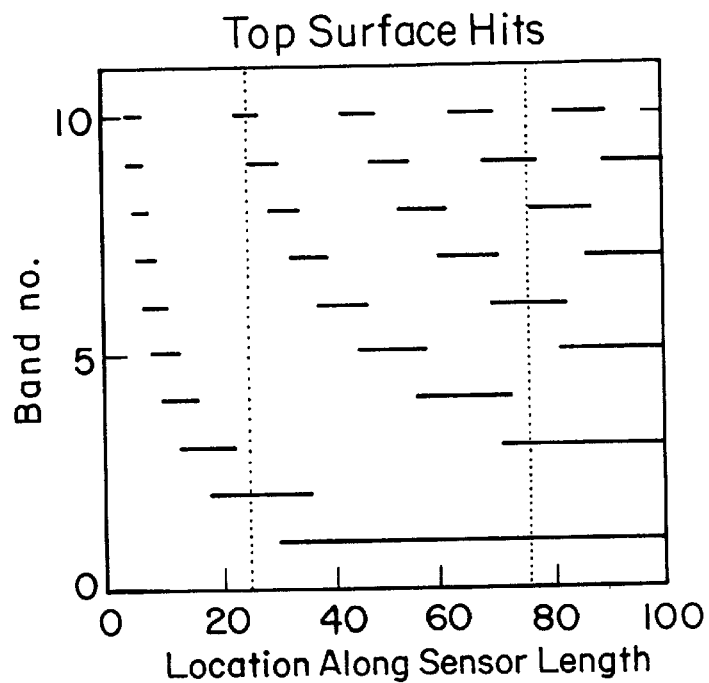
FIGS. 5A and B are graphs of folded lightpipe top (5A) and bottom (5B) surface reflections as a function of angular band number showing the location and size of illuminated spots on the top and bottom surfaces of the lightpipe for each angular band as horizontal solid line segments. A reflection extends from the beginning to end of the line segments. The location along the sensor length is indicated in percentage of total length.
Figure 5B:
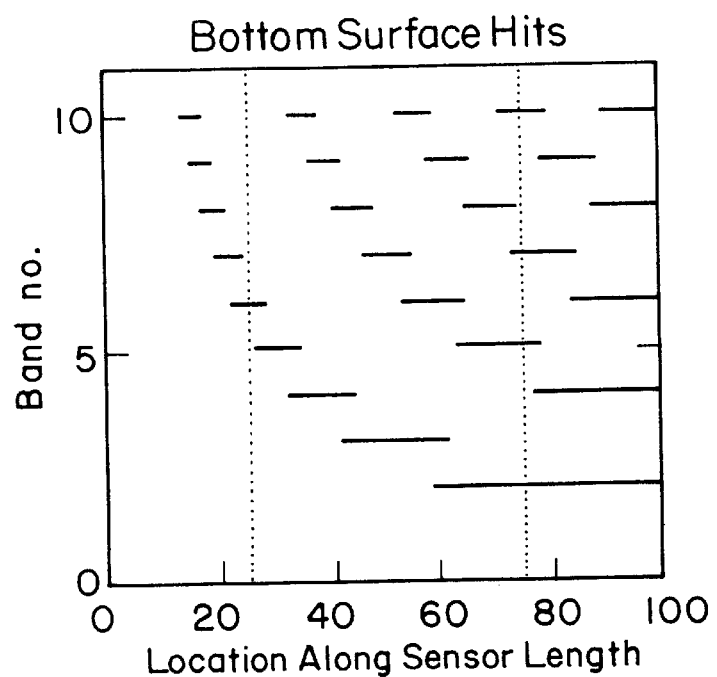

FIGS. 5A and 5B provide a graphs of the locations of reflections off of the top and bottom surfaces of a lightpipe of FIG. 2. The locations (in percent of lightpipe length) are plotted as a function of band number. These graphs are based on calculations that have been described in detail in U.S. patent application (Attorney Docket No. 89-95) filed Oct. 25, 1996 which is based on a U.S. provisional application Ser. No. 60/007,027 filed Oct. 25, 1995. This calculations can be used to optimize the location of a sensing area on the top or bottom of a lightpipe for a given application.

The patterns in FIGS. 5A and B can be used to optimize the sensing area (conductor or metal layer) locations and size for a specific sensing application. Some first order sensing applications require obtaining resonances from a maximum number of bands. In such a case, a band with partial or multiple reflections off the sensing film would be acceptable as long as a resonance was observed. For example, in measuring the dispersive RI, it is preferable to analyze as many different bands as possible each having a different resonance at different wavelengths to allow determination of RI at many wavelengths. In another example, many different components of a given sample can be simultaneously assessed using differential functionalization of the SPR sensing areas (i.e., providing different reactive layers) on a lightpipe sensor surface. In this case, each exiting angular band would carry information about a different component (analyte) in the sample. In yet another example, having the ability to analyze multiple bands sensing the same sample or analyte provides several benefits. It allows an internal confirmation or check of a given measurement, thus avoiding spurious readings that might occur on a single channel. Further, since the higher the band angle, the greater its sensitivity and the less its dynamic range, the availability of multiple bands allows a selection of the highest sensitivity channel for a given sample.

Other applications might require high sensitivity of $\Delta\lambda_{SPR}/\lambda RI$ in a limited number of bands. These applications would benefit by designing the sensor to operate at the highest angle possible, with only one or two reflections per band. For example, a bioassay for an analyte present at a very low concentration, where the dynamic range was known, preferably would be done employing a single band with as high a sensitivity as possible.

If light is introduced into the lightpipe of FIGS. 2 and 3 symmetrically at angles above and below the axis of the lightpipe, the light focused on the lightpipe input face from below the lightpipe axis will also give a pattern of angular bands on exiting the lightpipe. The banded output pattern from light of angles below the axis will be the complementary pattern of that from light focused at angles from above the axis. If the lightpipe planar surfaces are perfectly flat and, if the exit end is polished perfectly flat, the complimentary pattern will fill the gaps (shown in FIG. 2) between the light bands in the pattern generated by light focused from above the axis when viewed near the output face of the lightpipe. Since in practice a lightpipe is not perfect in dimensions and flatness, there will be some overlap of exiting bands in the symmetric light input configuration. When symmetric light input is used in a lightpipe configuration, the exit optics and detection scheme used must take into account potential overlap of the angular output bands. The distinction between asymmetric and symmetric illumination of a lightpipe is discussed in detail in U.S. provisional applications Ser. No. 60/007,027 filed Oct. 25, 1995; Ser. No. 60/005,878 filed Oct. 26, 1995 and corresponding U.S. patent application Ser. No. 08/758,360 filed Oct. 26, 1996.

The term "asymmetric light input" is used herein when light entering the lightpipe at a range of angles asymmetric with respect to that plane and consists of a range of angles either below that plane or above that plane, but not both. In contrast, as discussed below, "symmetrical light input" refers to light input that is symmetrical with respect to the axis plane with a range of angles both above and below the plane.

Figure 6:
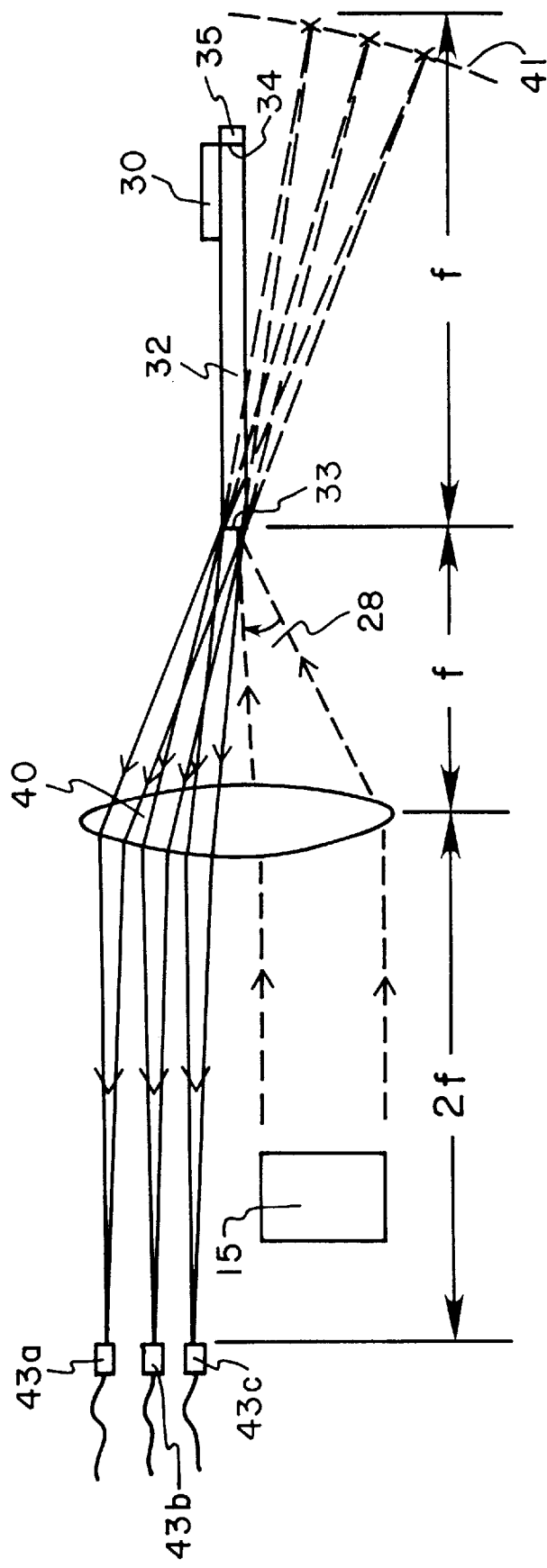
FIG. 6 is a schematic drawing not necessarily drawn to scale of a folded lightpipe configuration of this invention. Light is asymmetrically input into the lightpipe from below the lightpipe optical axis and angular bands exiting the lightpipe above the lightpipe axis are collected for detection.

The folded lightpipe configuration of FIG. 6 (side view only) illustrates the use of a telecentric lens (40) for collecting, redirecting angular bands so that they are substantially parallel to the lightpipe axis and can be directed into a detector, for example via the fiber optic pick ups (43a, b or c). The telecentric lens is positioned on-axis. The same telecentric lens functions simultaneously to couple input light from light source 15 into the lightpipe asymmetrically at a range of angles (28).

The operation of telecentric lens is described in (Smith, W. J. (1990) *Modern Optical Engineering, The Design of Optical Systems*, 2nd ed., McGraw Hill, N.Y.). A telecentric system comprises a telecentric lens which may itself have several components. A telecentric lens is a lens in which an aperture stop (the telecentric stop) is located at the front focus and results in the chief rays of light passing through the lens being substantially parallel to the optic axis of the lens in image space. In the illustrated telecentric system, a cylindrical lens simultaneously redirects and focuses output bands onto a plane perpendicular to the lens axis and makes the bands substantially parallel to the optical axis of the lens. A spherical lens placed in an analogous telecentric structure (i.e., a spherical telecentric lens) simultaneously redirects and focuses the light from the bands (as would be seen from both the side and top views of the substrate, not shown). A telecentric lens images output bands into individual spots or lines, so that a detection device, e.g., fiber optic pickup, photodetector or entrance slit for a spectrograph, can be placed at the image location (about 2 focal lengths from the telecentric lens, 2f) to capture the signal with minimal effects from defocus. The telecentric lens is positioned one focal length from the output end of the lightpipe sensor so that the output face of the sensor acts as a telecentric stop. Alternatively, albeit with significant light loss, a separate output aperture can be provided to reduce the angular width of each band. Since each band of light passes through an aperture at the focus of the lens, the path of each output band is straightened out to be substantially parallel to the optical axis of the lens.

The individual bands exiting the lightpipe can be considered to originate from locations along a virtual arc (41, in FIG. 6), so that each band will come to a focus some distance behind (2f) the telecentric lens. When the telecentric lens has a focal length approximately equal to the distance between the virtual source origin to the end of the lightpipe, the size of the output focus and spot will be comparable to the size of the incident spot. This choice of focal length for the lens is preferred for efficient light collection by the detection optics.

The telecentric lens is preferably chosen so that the field curvature of the lens is matched to the profile of the virtual arc of sources (Smith, W. J. (1990) supra and Optics Guide 5, Melles Griot Catalog (1990)). When the condition is met, all the bands will focus at a common plane perpendicular to the optical axis. This choice of lens is particularly useful and preferred for capturing multiple bands of light at the same time. It is also preferred when capturing multiple bands that the lens is chosen and positioned so that the separation between the center of each band is constant. Then the focus of the light into the detector optics can be adjusted by moving the structure (sensor and lens) along the axis without the need for transverse adjustment.

There are limitations to this telecentric system. There is a mismatch between $R_{LP}$ and $R_{petzval}$ such that $R_{petzval} \approx 1.5 R_{LP}$. This means that, in practice, the output image in these configurations will not land on a flat plane but will have a slight residual curvature toward the lens. Ray tracing this system has made it clear than an achromatic lens must be used to control the blur in the image spots. The practical limit on the diameter/focal length ratio of achromatic lenses limits the bands that can be collected to those with internal incidence angles less than $\approx 17°$. Since the sensitivity of an SPR sensor is related to the angle of the incident light, limiting the maximum band angle constrains the maximum obtainable sensitivity.

In FIG. 6, the optical axis of the telecentric lens is aligned with the optic axis of the lightpipe (on-axis). The lens can be employed in other output optical geometries for capture of angular bands. For example, the telecentric lens axis can be aligned with the center ray of any angular output band to capture adjacent bands. In this case, the telecentric lens will redirect and focus the bands passing through it to make them substantially parallel to the optical axis of the lens (i.e., parallel to the direction of the output band to which the lens is aligned).

The advantage of the telecentric configuration is the redirection and focusing of the light can be accomplished simultaneously by a single lens and that the bands are straightened out to be parallel to the optical axis. In the case of the folded light pipe sensor, a single lens can be used to both focus the incident light and redirect the return light is as shown in the configuration of FIGS. 7A(top) and FIG. 7B(side). The incident light is collimated and made parallel to optical axis by spherical collimator 47, shown in FIG. 7B, but not in FIG. 7A. Light is then focused onto the input/output face of the lightpipe by the telecentric lens 40.

The design constraints for the folded substrate are identical to that of the unfolded, with the same concerns for matching the lens to the profile of the arc and collecting the signal light. The only notable exception is the locating the metal film, which would be equivalent to symmetrical patches on both sides of the unfolded configuration. The top view of the sensor of FIG. 7A shows that light is collimated while traveling through the sensor. This is accomplished using a telecentric interface lens that is a cylindrical lens, oriented to focus light in the side view and not affect the top view, creating a line image on the entrance face of the sensor. As shown in the side view in FIG. 7B, different spherical 47 and cylindrical 45 lenses can be used above and below the optical axis in order to facilitate the separate requirements of the input and return beams. The design constraint of this configuration, beyond the ones previously discussed, is to pick the focal length of the cylindrical imaging lens 47 and the spacing between the elements so that the return light is imaged into the pick-up optics without undue amounts of blur causing aberrations.

The possibility of a single interface lens allows a very simple and robust instrument and probe to be designed around the folded light pipe sensor.

Figure 8:
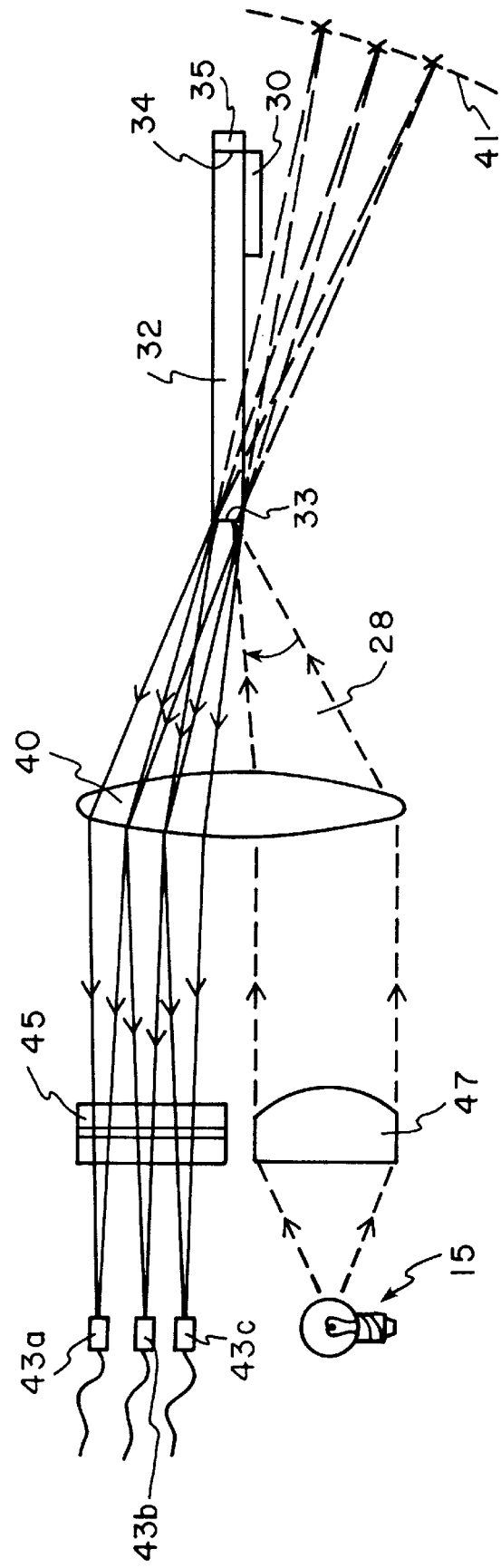
FIG. 8 is a side view not necessarily drawn to scale of an alternative folded lightpipe configuration with light input from above the lightpipe axis. This configuration is preferred.

Several different configurations of folded lightpipe configurations are provide in FIGS. 8, 9A and B and 10A and B.

Figure 7B:
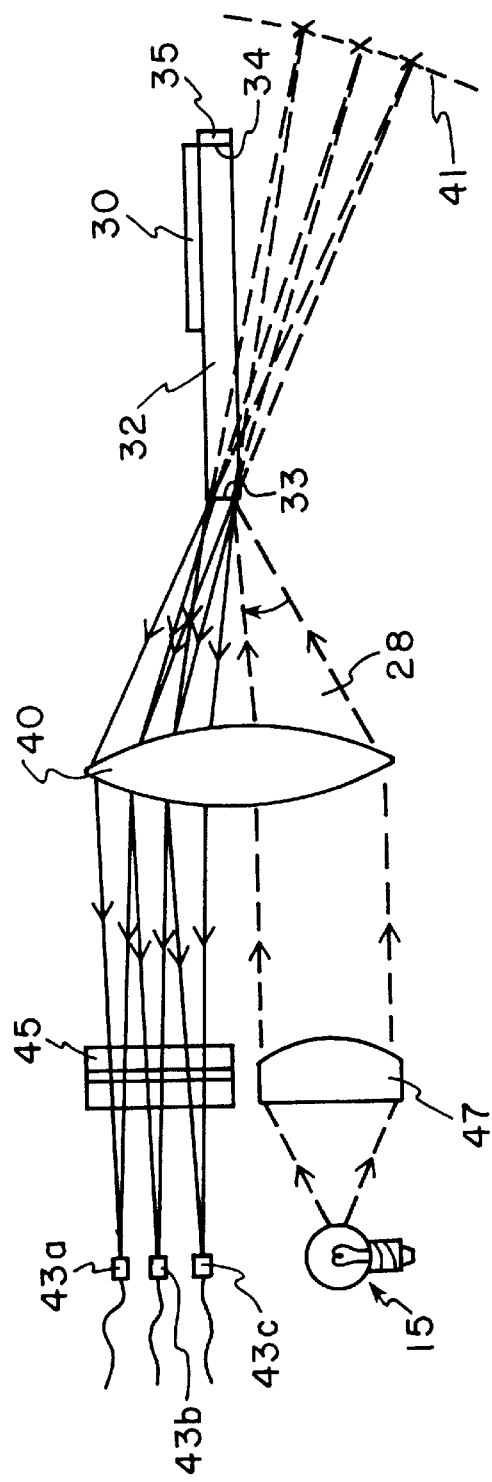
FIG. 7B is a side view of the lightpipe of FIG. 7A. Light input is from below the axis of the lightpipe.

The sensor configuration of FIG. 8 is identical to that of FIG. 7B except that light is input into the lightpipe from the opposite side of the lightpipe axis. (By the convention used herein for naming the top surface of the lightpipe, light enters from above in FIG. 8). It has been found that the light input configuration of this figure is preferred.

The sensor configuration shown in FIGS. 9A and B is similar to that of FIGS. 7A and B. Instead of a line focus at the input, a spherical telecentric lens (42) can be used to create a focus spot at the input face of the sensor. Therefore, the top view of FIG. 9A shows the light diverging as it travels through the sensor. Contemplating the unfolded top view shown in dotted lines, the light refracts while leaving the sensor, resulting in a virtual origin along the same arc (41) as shown in FIG. 9B. A spherical telecentric interface lens 42 redirects and images the return light in both views simultaneously. The incident illumination requires some form of lensing to provide collimated light below the optical axis to be incident on the back side of the telecentric relay lens.

The design of this optical configuration is adapted for light that is diverging as it travels through the sensor. If the sensing film was deposited in a rectangular patch as in FIG. 7B, different diverging angles through the sensor would travel different path lengths to the film and then interact with the film for different lengths. This could compromise the quality of the return signal by having multiple reflection of the sensing film. One way to solve this would be to use a curved patch of sensing 50 film, as shown in FIG. 9A. Unfortunately, the light in the folded configuration will also encounter the sensing film on its return trip, but now the film will be curved in the wrong direction relative to the divergence of the light. Since the odd bands of light are ignored in this configuration (and all of the configurations illustrated), the metal location is designed so that only the odd bands are affected by partial reflections off the sensing film. A version of this sensor configuration with simple straight patches of metallic sensing films has been built and demonstrated and was found to function as desired.

Figure 10A:
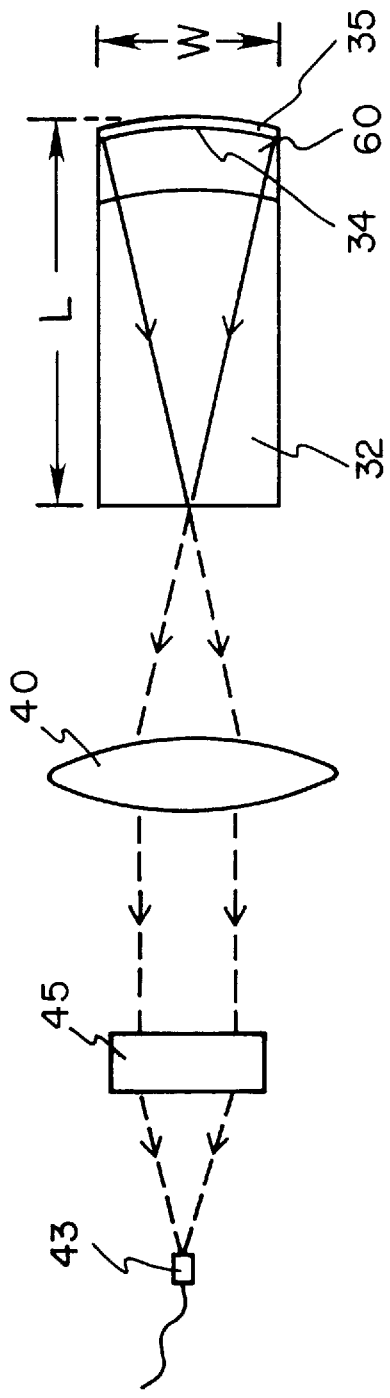
FIG. 10A is a top view and FIG. 10B a side view of an alternative folded lightpipe configuration of this invention (not necessarily drawn to scale). The mirrored distal end of the lightpipe is cut to a curve having a constant radius (e.g., of L or 2L). The sensing area on the lightpipe surface is also curved.
Figure 10B:
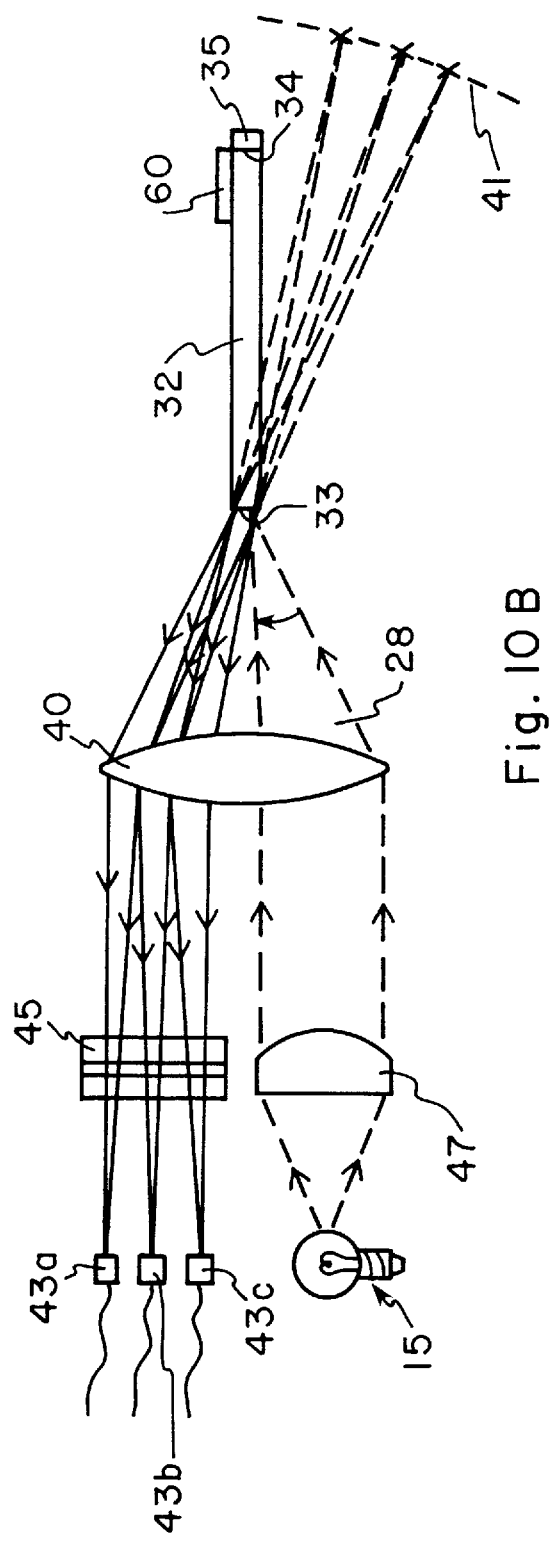

The configurations in FIGS. 7A and B and 9A and B both utilize a rectangular sensor substrate. The third configuration, shown in FIG. 10A and B has a radius cut into the distal end of the lightpipe. The unfolded equivalent (not shown) is a cylindrical lens placed in the middle of the sensor. The radius of the mirror can be chosen to return collimated light if a point source is imaged on to the slide or a point focus with collimated input. However, if the radius of the mirror is cut to be the same as the length of the sensor (L), then a point source input will be auto-collimated back to a point source at the output. If a curved patch of sensing film 60 is utilized, then the problem of variable path lengths with diverging light is solved, although at the expense and difficulty of creating a curved mirror at the end of the sensor. As with the design in FIG. 7B, this configuration requires a cylindrical lens 45 to image the return light into the pick-up optics.

To make a sensor equivalent to a white light fiber optic SPR sensor, the configuration is designed so that only one band is illuminated, collected and its wavelength reflection spectrum analyzed. The incident light should consist of a range of different wavelengths of light. If the illumination is a continuous source in the near infrared (near IR), it is common to normalize the signal by dividing by a reference spectrum to remove the effects of the lamp and detector. Changes in the conditions on the sensor surface will cause the reflection spectrum to change which can be monitored by tracking the location of the most attenuated wavelength in the reflection. However, it is not necessary to have continuous light, but if several line sources were used some form of regression analysis would have to be employed. It should be noted that wavelengths can be used that extend far into the IR, but this will require the use of other detector materials other than silicon based photodiodes.

As shown in FIGS. 6–10B, the return light can be collected by a fiber optic and relayed to some form of a spectrograph for analysis. Since all the configurations show return light imaged to a point, no extra optics would be needed to couple the signal into the fiber. Alternatively, the input of the spectrograph can be located directly at the primary focus, doing away with the relay fiber. If several bands are illuminated simultaneously and only a single band is collected, then it is possible to "tune" the response of the sensor by collecting different bands for analysis. This is possible because the higher angle bands have greater sensitivity but less dynamic range.

Although a fiber optic SPR sensor is considered a $0^{th}$ order sensor, the light pipe sensor is capable of $1^{st}$ order sensing. To accomplish this, several bands need to be collected simultaneously. This can be as easy as including several collection fibers as shown in FIGS. 6–10B. Alternatively, a two-dimensional spectrograph can be included at the primary focus instead of the relay fibers.

A third way for read-out exists which involves quasi-monochromatic illumination instead of using "white" light. In this method, a laser diode (preferably), or a LED or band pass filtered bulb could be employed. If the sensor is designed so that many bands are illuminated at the same time, then a version of the standard monochromatic angle modulated SPR sensor can be constructed. By using an array of photodiodes such that each detector intercepts a specific band of return light, each photodiode would produce an intensity value corresponding to a discrete angle of incidence. Since some bands will probably have double or partial reflections, this design would place constraints on the position of the sensing film. Unlike standard angle modulated SPR analysis, the existence of partial and multiple reflections off the sensing film would require sophisticated signal analysis schemes in order to conduct measurements and calibrations.

The SPR sensor configurations of this invention can be operated in either angular modulation mode, wavelength modulation mode or a combination of both modes of operation. The light sources employed with the sensor can be monochromatic or more preferably are non-monochromatic. A monochromatic light source provides light of substantially one wavelength. A non-monochromatic light source is any light source that provides light of more than one wavelength, i.e., any light source that provides multiple wavelengths. Preferably, the non-monochromatic source provides a range of wavelengths of light sufficiently broad to encompass the SPR spectrum of the sample. A black body radiation source or one or more broad spectrum light emitting diodes are, for example, suitable multi-wavelength light sources.

Alternatively, two or more discrete wavelengths of light, e.g., from distinct light sources, can be employed in the sensor of this invention.

In alternative embodiments of the lightpipe of this invention, diffraction gratings fabricated on the planar lightpipe can be employed at the input and output ends of the SPR lightpipe sensors to couple incident monochromatic light into or reflected monochromatic light out of the lightpipe. A diffraction grating can be introduced onto the bottom or top surface of the lightpipe near either the input or output end, or at both ends. The grating is created in or on the substrate material of the lightpipe by conventional methods, for example lithography and etching techniques standard in the semiconductor industry. Light is coupled into the lightpipe at desired transmission angles by focusing light at the appropriate incidence angles onto the input grating.

The folded planar lightpipe sensors of this invention comprise a sensing area adhered to the external top surface of the lightpipe. Detection of a sample or a given species in a sample by the lightpipe SPR sensor is made, in part, by contacting the sensing area of the lightpipe with the sample. The sensing area is prepared by adherence of an SPR-supporting conductive layer to a selected area on an external longitudinal surface of the lightpipe. The position and length of the sensing area is selected to optimize the sensor for a given application.

The lightpipes of the SPR sensors of this invention are fabricated from a material that is transparent or semi-transparent to the range of wavelengths of light to be employed in a given application. Useful substrates include glasses, crystals, plastics and polymers. To insure TIR in the lightpipe, e.g., along the length of the lightpipe, the lightpipe is optionally provided with a cladding layer having an index of refraction different from that of the lightpipe substrate. The cladding is provided over the entire lightpipe (except for sensing area) or over selected portions of the lightpipe. Those of ordinary skill in the art know and understand how to select and can readily select a lightpipe substrate appropriate for a given application. Those of ordinary skill in the art also know how to select and can readily select an appropriate cladding layer for a given application and substrate material.

The sensing area comprises one or more layers which together support SPR. The sensing area comprises an SPR-supporting conductive layer. This layer may be a conductor, e.g., a metal layer that supports SPR or a semiconductor layer that supports SPR. Semiconductors useful in the conductive layer include silicon and germanium. Alternatively, conductive polymers can be used in the conductive layer.

The conductive layer can be a "SPR-supporting metal layer" which is herein means a highly-reflective metal that supports SPR at the metal/sample interface and has a permittivity constant wherein the real part of the permittivity is negative and its magnitude is greater than the magnitude of the imaginary part. For wavelengths in the visible and near-infrared (i.e., 400 nm-1000 nm), both silver and gold satisfy this criterion. The SPR supporting metal can also be a mixture of one or more metals or be composed of sequential layers of different metals. If the wavelength range utilized extends into the infrared, other metals, such as aluminum, copper and tantalum, may also be used.

Preferably the SPR-supporting conductive layer, e.g., the metal layer, is adhered to the lightpipe surface to a thickness which will optimize the measured resonance curve, i.e., to a thickness which makes the SPR resonance spectrum both deep and sharp, between about 400 Å to 700 Å thick. When the SPR-supporting metal layer is made of silver, the layer thickness preferably is between about 500 Å to 550 Å thick. Layers of silver thinner than about 400 Å result in substantially shallow and broadened resonances, and layers thicker than about 600 Å will result in significant diminishment or disappearance of the resonance feature. The range of thicknesses for gold SPR-supporting layers are also 400–700 Å, preferably 500–600 Å. Gold is preferred because of its inertness and resistance to oxidation. SPR-supporting metal layers can be prepared with sequential layers of different metals, for example, a base layer of silver combined with an upper layer of the gold for a total double layer thickness of between about 400 Å to about 700 Å. One of ordinary skill in the art can readily determine the appropriate thickness of the SPR supporting metal layer for a given lightpipe sensor application by varying the metal layer thickness to optimize the resonance curve.

SPR-supporting conductive layers are adhered to the lightpipe surface by methods known in the art. An SPR supporting metal layer can be adhered by standard procedures, including vacuum deposition, electron beam deposition, sputtering, chemical vapor deposition and the like. Layer thickness is controlled by well-known methods, for example employing a quartz crystal oscillator or other suitable thickness monitor. U.S. Pat. Nos. 4,997,278, 5,064, 619, 5,351,127, and 5,485,277, for example, disclose, reference or summarize methods for adherence of an SPR-supporting metal layer.

Prior to adherence or deposition of the conducting layer a base or adherence layer is optionally applied to the substrate (here, lightpipe) surface. The adherence layer is typically a metal layer, such as chromium, nickel, platinum or titanium, less than about 50 Å thick, and more preferably about 20 Å thick.

The sensing area optionally contains one or more additional layers adhered to the SPR supporting conductive layer to yield a change in the effective refractive indices detectable by the sensor. Such additional layers can include a dynamic range-controlling layer, a reactive layer, a protective overlayer or any combination thereof. A variety of techniques are known and available to those in the art to provide dynamic range-controlling layers, reactive layers and protective layers in an SPR sensing area.

A "dynamic range-controlling layer" is a layer adhered to the SPR supporting conductive layer to alter the dynamic range of the SPR sensor. This layer has an index of refraction different (either higher or lower) than that of the SPR-supporting layer. For example, adherence of a layer of higher refractive index to the index of the substrate will extend the dynamic range of the sensor to include lower RI values. For example, U.S. Pat. No. 5,327,225, describes the use of an overlayer of relatively high refractive index material, specifically SiO, on a fiber SPR sensor with a silver SPR-supporting layer to shift the dynamic range of the sensor to a lower RI value.

A "reactive layer" is an optional layer in the sensing area which interacts with a sample or an analyte species in the sample such that the effective refractive index detected by the sensor is altered. The addition of the reactive layer permits the manufacture of an SPR sensor which is more sensitive or selective for a sample (or analyte in a sample). Suitable reactive layers include those used in biological sensors, e.g., an antigen, antibody, nucleic acid or protein bound to the SPR supporting metal layer. This type of reactive layer will selectively bind a species in the sample, for example, a cognate antibody or antigen or complementary nucleic acid in the sample, increasing the thickness of the reactive layer and causing a shift in the effective refractive index measured by the sensor. Most generally, suitable reactive layers are altered in some way by contact with the sample so that the effective refractive index as measured by the sensor is changed. Reactive layers also include sol-gel films and polymer coatings. Reactive layers can be adhered to the SPR-supporting conductive layer or to an overlayer on the conducting layer. The reactive layer should interface with the sample solution.

U.S. Pat. Nos. 5,055,265 and 5,478,755 relate to SPR sensor configurations utilizing so-called "long-range SPR" (LRSPR). LRSPR differs from traditional SPR in the use of a distinct layering in the SPR sensing area. LRSPR employs a thinner conducting layer (100–200 Å) than in traditional SPR (500–600 Å). An LRSPR sensing area is fabricated by first depositing a thin dielectric layer on the transparent substrate after which the thin conducting layer is deposited. The metal layer can directly contact the dielectric sample, or a reactive layer can be laid down upon the conductive layer. LRSPR in general provides increased sensitivity. The sensor configurations of this invention can be employed for LRSPR by appropriate adjustment of the layers of the sensing areas.

A number of methods have been described, are known and available to those of ordinary skill in the art, for the formation of reactive layers with sensitivity to a variety of biological or chemical species. Formation of the reactive layer on a metal layer may require an intermediate thin layer of material to passivate the metal or protect ligands in the reactive layer from reaction with the metal; For example, U.S. Pat. Nos. 4,844,613, 5,327,225, 5,485,277, and 5,492,840 disclose or summarize methods for preparation of such reactive layers in SPR sensors.

An SPR sensor of this invention can be configured with one or more sensing areas. One or more active sensing areas (those capable of detecting changes in RI of a sample) and one or more reference sensing areas can be provided in an SPR sensor. Active sensing areas in an SPR sensor can be provided with different reactive layers (e.g., can be functionalized for interaction with different biological or chemical species or functionalized differently for interaction with the same biological or chemical species), different over- or underlayers, different dynamic range-controlling layers and/or combinations thereof.

A sensing area on a planar lightpipe of this invention can, for example, be subdivided into lateral regions across its width to provide separate sensing channels, including reference channels and sensing channels with different analyte selectivities. Differential sensitivity can be provided by use of different reactive layers. One of the lateral regions of the lightpipe can function as a reference for other activated and functionalized sensor channels. If the reference region is not functionalized or activated (i.e., no reactive layer provided) it will serve to track temperature changes, variations in the light source and signal due to nonspecific adsorption of the analyte. Alternatively, the reference area can be coated with a thick layer of a reference material (a dielectric) so that it does not react to the sample and will serve to track temperature changes or variation in the light source.

A sensing area or a portion of sensing area can also comprise an overlayer that protects or insulates the SPR-supporting layer from changes in the RI of the sample. For example, a reference sensing area can be made by providing a sufficiently thick overlayer of a dielectric material, such as a cured epoxy on the SPR-supporting layer. The reference sensing area then senses, and be used to correct for, temperature variations, light source variations and related instrumental variations.

Figure 11A:
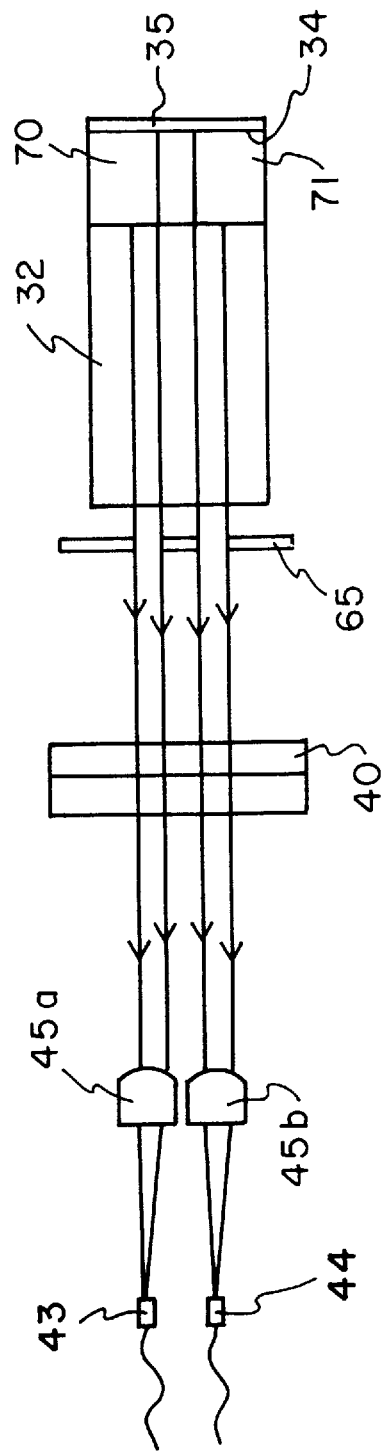
FIGS. 11A and 11b illustrate a dual-channel folded lightpipe sensor of this invention (not necessarily drawn to scale).
Figure 11B:
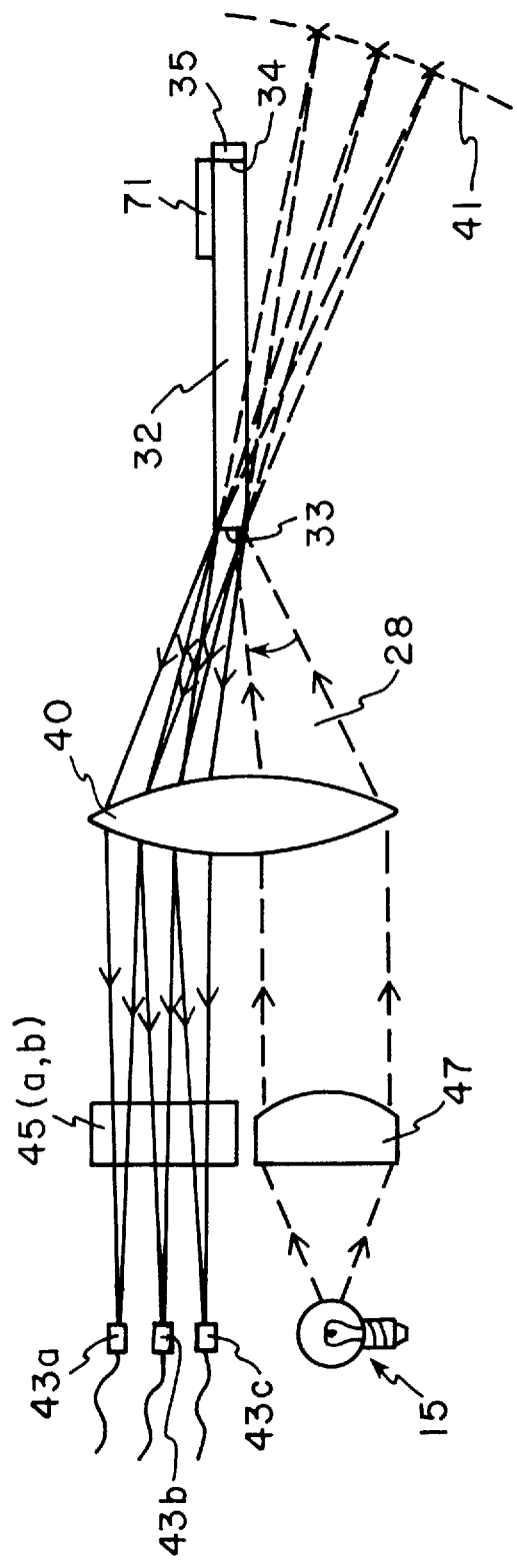

FIGS. 11A and 11b illustrate a dual-channel folded lightpipe sensor of this invention. FIG. 11A is a top view and FIG. 11B is a side view. The sensing area on the top surface of the planar lightpipe is divided into two parts along the width of the top surface, which constitute two different sensor channels (70 and 71). Both channels are fabricated on the same sensor substrate, for example on a standard microscope slide, and have an identical SPR-supporting conductor layer and optional adherence layer. The length and positioning of the sensing areas are selected as discussed above. Only one of the channels is active for sensing particular species in the sample solution. The sensing areas differ in the functionalization of the conducting surface for interaction with specific species in the sample. For example, only one of the sensing areas (70) contains a reactive layer, as described above, which interacts with a specific species in solution causing a shift in SPR resonance. The other sensing area, the reference sensor channel (71), is inactive to such interactions and SPR on this sensor channel is a function both of the effective RI of the sample and non-specific absorption events.

The configuration of FIGS. 11A and 11B is similar to that of FIG. 7B. The optional aperture 65 (shown in FIG. 11A, but not shown in FIG. 11B) has been added to the system to facilitate discrimination of light in the different channels. The detection optics include a telecentric lens (40) to redirect the angular bands and cylindrical lenses (like 45(*a*) and 45(*b*)) to image individual bands into fiber pick ups (43 *a,b,c* or 44 *a,b,c*). As illustrated, the detection optics can be configured to conduct individual bands into individual fiber pick ups which ultimately lead to a detector. Other detector configuration are available. For example, an array of fiber optic pick ups can be provided to detect a plurality of angular bands, or one (or several) fiber optic pick ups which can be adjusted to pick up any desired angular bands can be provided.

As long as the functionalized (reactive) layer in the active layer is thin (generally these layers are only a few monolayers thick), the temperature dependence of the two channels is substantially the same. In the configuration of FIG. 11B the SPR channels share the same light source and detector system. Subtraction of the SPR signals (the reference SPR from the active sensor) yields the temperature independent system response to the interactive species. This referencing mechanism also removes the effects of light source fluctuations and system losses.

In an alternative multi-channel sensor, the reference sensing area and any active sensing areas are formed with the identical SPR-supporting conducting layer and the same adherence layer (if any). An overlayer is then applied to the reference sensing area to provide interaction with a layer of constant RI. For example, a relatively thick layer of cured epoxy can be used to overlay the SPR-supporting layer. The reference sensing area in this case does not respond to changes in sample RI or to any specific binding of analytes that might occur on the active sensing area(s) of the sensor. The reference sensing area responds to changes in temperature, light source and other possible instrumental variations.

In a multi-channel lightpipe sensor, the SPR signals from each channel can be independently collected and measured. For example, SPR signals from two adjacent channels shown in FIG. 11B can be individually collected using fiber couplers (43*a* and 43*b*) into adjacent fibers and then transmitted into the same spectrograph, one at a time, periodically through a fiber switch under time control. Switching time and spectrograph analysis in such a system can be synchronized by a computer. Alternatively, a two-channel (or multiple channel) spectrograph can be utilized. The on-site and real time temperature information of the whole sensor system, thus, can be collected for the reference signal and extracted from the active SPR signal by conventional signal processing methods.

In practice, the refractive index along the sensing interface in an SPR sensor is temperature dependent, as are the characteristics of the light source and the detector in the sensor system. Temperature fluctuations lead to variation in the SPR excitation condition and cause undesirable shifts in SPR wavelength. Thus, temperature compensation of the SPR sensor can significantly improve the accuracy of sensor measurements. One way to deal with temperature variation is provide a means for keeping the sensor at a constant known temperature (e.g., temperature control). This may not be practical in certain sensor applications. Alternatively, a sensor can be temperature compensated by developing a complex algorithm to allow correction of sensors measurements as a function of temperature variations. A third method for accounting for temperature variations to improve sensor accuracy is to incorporate a reference SPR signal as the compensation mechanism. SPR sensor configurations employing the planar lightpipe of this invention are readily adapted to include multiple sensor channels, one of which can be employed as a reference for temperature compensation.

Figure 12A:
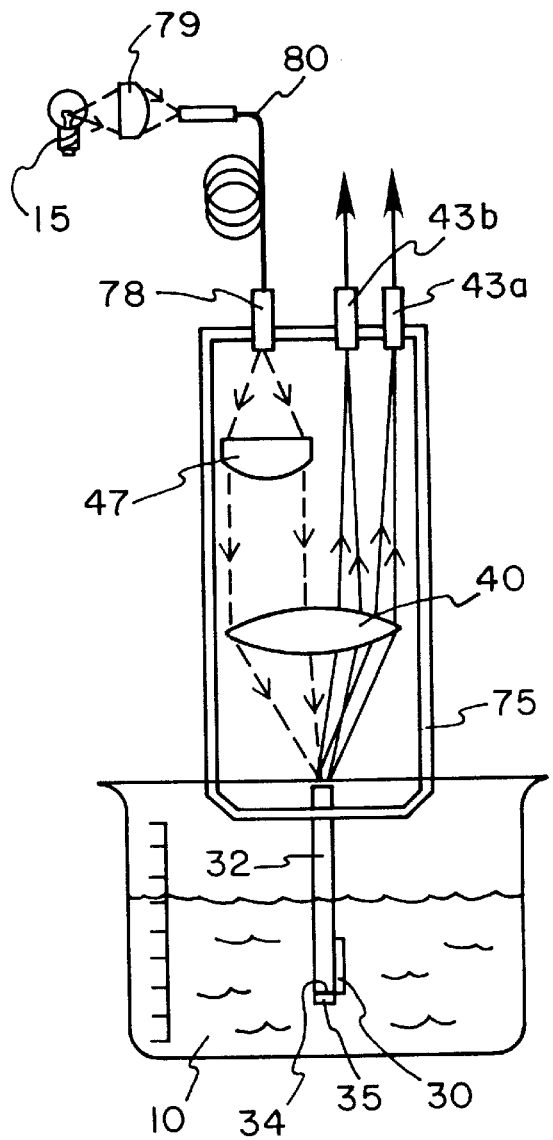
FIG. 12A is a drawing of a SPR lightpipe probe configuration.

FIG. 12A is a drawing of a SPR lightpipe probe configuration. An SPR lightpipe probe has some significant advantages over fiber optic probes because lightpipe sensors can have greater sensitivity, flexible dynamic range, lower cost and they can be directly multiplexed. FIG. 12A illustrates a probe housing 75 which carries the lightpipe sensor 32 and the input and output optics. Light is input via a fiber optic cable 80, through appropriate fiber couplers 78. Light from light source 15 is coupled into fiber 80 with an appropriate lens (79). The output of the angular bands is picked up with a different fiber or fibers (two fiber pick ups 43(*a*) and 43(*b*) are shown). These output fibers conduct light to a detector or detectors (not shown). Although the probe in FIG. 12A is shown immersed in a sample solution (10), it is also possible to place the probe tip, i.e., the lower portion of the folded lightpipe carrying sensing area 30 in a moving stream of sample such as a flow cell or even a large transfer pipe in an industrial application. This allows the probe to monitor static situations, like biochemical reactions in a beaker, or to monitor dynamic environments, such as refractive index monitoring of samples in a flowing process control application.

Figure 12B:
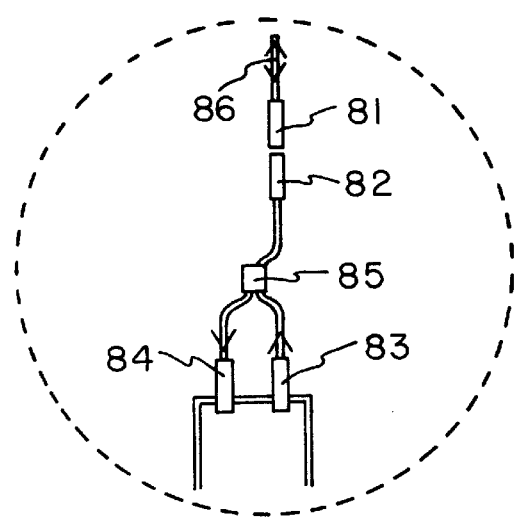
FIG. 12B is a drawing of a modified fiber optic light input/output configuration for use with the probe of FIG. 12A.

The probe schematic in FIG. 12A is only one potential embodiment of the SPR lightpipe probe. The simple modification shown in FIG. 12B allows the probe to be used with the single fiber optical spectrograph commonly used with a fiber optic SPR sensor. FIG. 12B shows fiber optic light input/output configuration for use with the probe of FIG. 12A. A 2:1 junction 85 is used to split part of the incident light traveling outbound from the spectrograph to be routed into the input port (84) of the lightpipe probe. The return signal is routed through fiber pick up (83) and then through the 2:1 splitter (85) back to the spectrograph for analysis. The fiber optic light input/output configuration has appropriate fiber couplers illustrated as 81, 82 and 86 for attachment to various detector configurations. The 2:1 splitter can be a simple single to double fiber butt joint, a fiber optic coupler or a bulk optic beam splitter arrangement.

Figure 12C:
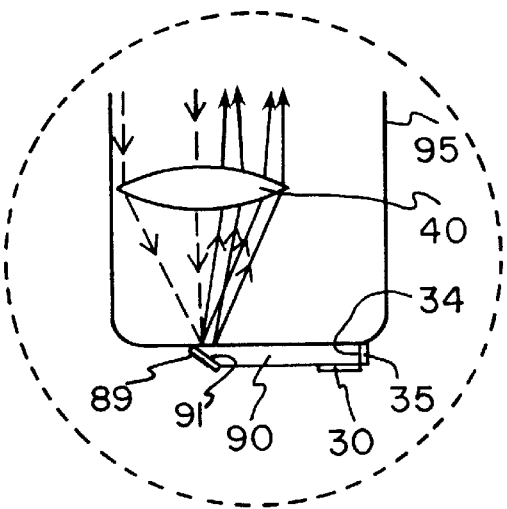
FIG. 12C shows another embodiment of a folded lightpipe probe. In this configuration, the sensor is constructed with a 45° angle at the input/output end. These figures are not necessarily drawn to scale.

FIG. 12C shows another embodiment of the folded lightpipe probe. In this configuration, the sensor is constructed with a 45° angle at the input/output end 91. This allows the sensor to be protected by laying the substrate flat against the end of probe casing 95. This "bent" lightpipe probe design is optically equivalent to the "straight" design in all respects. The 45° face can be left bare relying upon total internal reflection to redirect the light into the lightpipe or the face can be coated with a mirror as illustrated (89).

Figure 13:
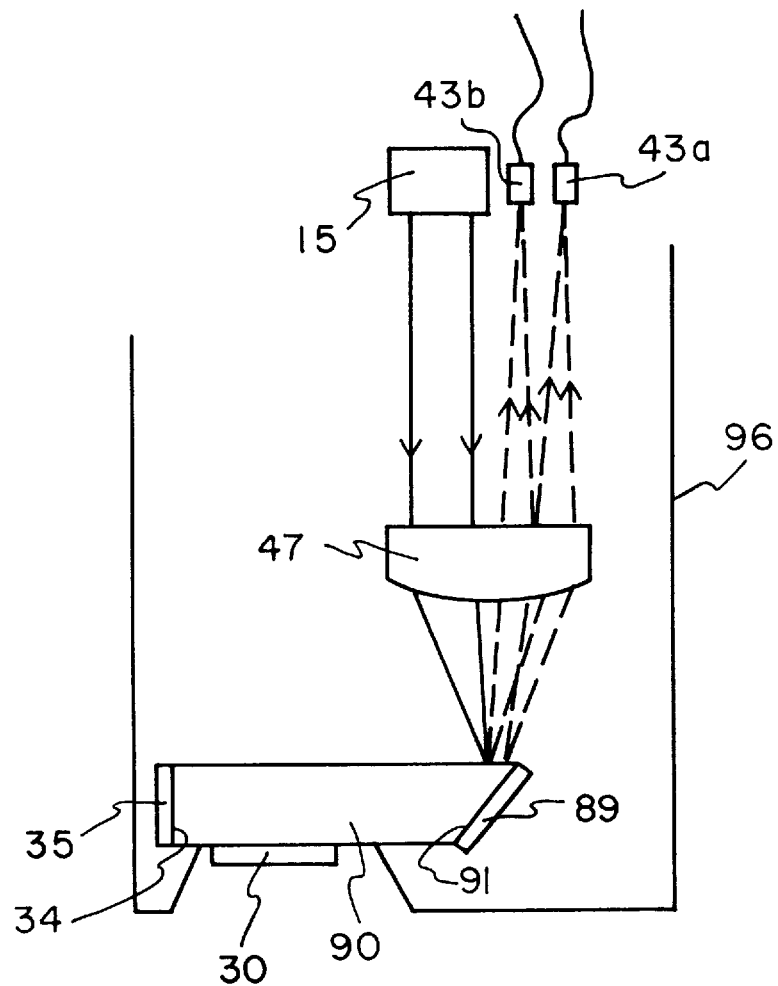
FIG. 13 illustrates yet another embodiment of the folded lightpipe probe (not necessarily drawn to scale).

FIG. 13 illustrates yet another embodiment of the folded lightpipe probe. In this configuration the lightpipe sensor (90) and its optics are protected within the probe casing 96. The figure illustrates the light source 15 with in the probe and fiber pick ups 43*a* and *b* for conducting output to a detector outside of the probe. The light source can be external to the probe casing as well. The probe casing has an opening into which the sensing area 30 of the probe extends for contact with sample solutions. Note that the sensing area need not be placed at the distal end 34 of the lightpipe. The walls of the probe casing extend outward around the sensing surface of the probe to protect it yet allowing sample to contact the sensing surface.

Figure 14A:
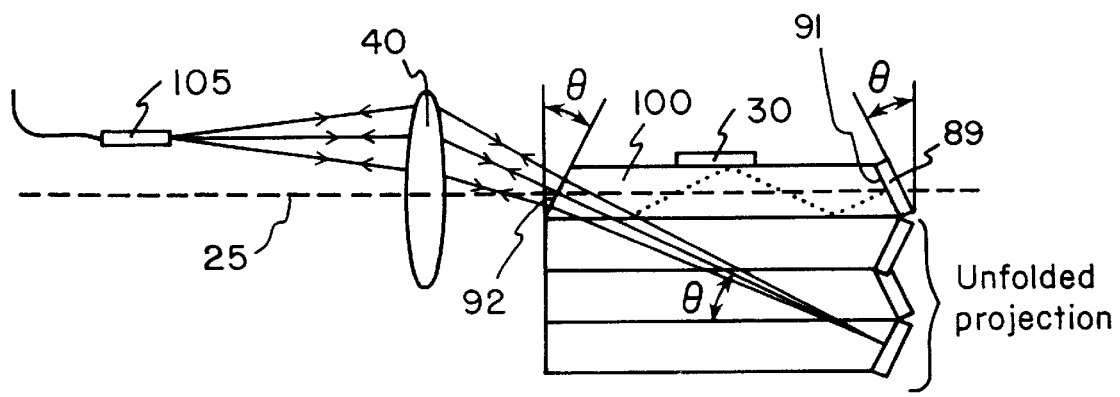
FIGS. 14A and 14B are schematic drawings not necessarily drawn to scale of single-fiber (for both input and output) auto-collimation configurations of folded lightpipe sensors or probes. Each of these configurations is readily adapted to the probe device configuration of FIG. 12A.
Figure 14B:
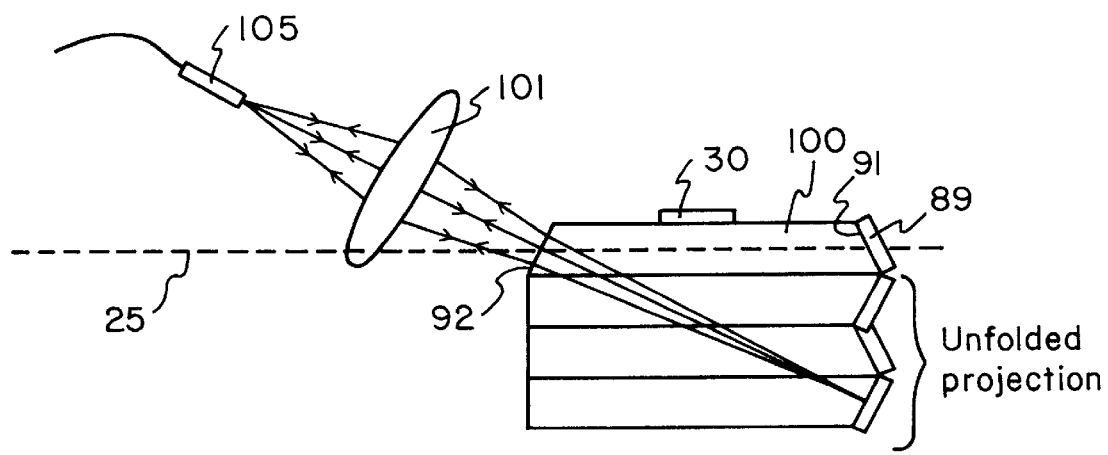
Figure 15:
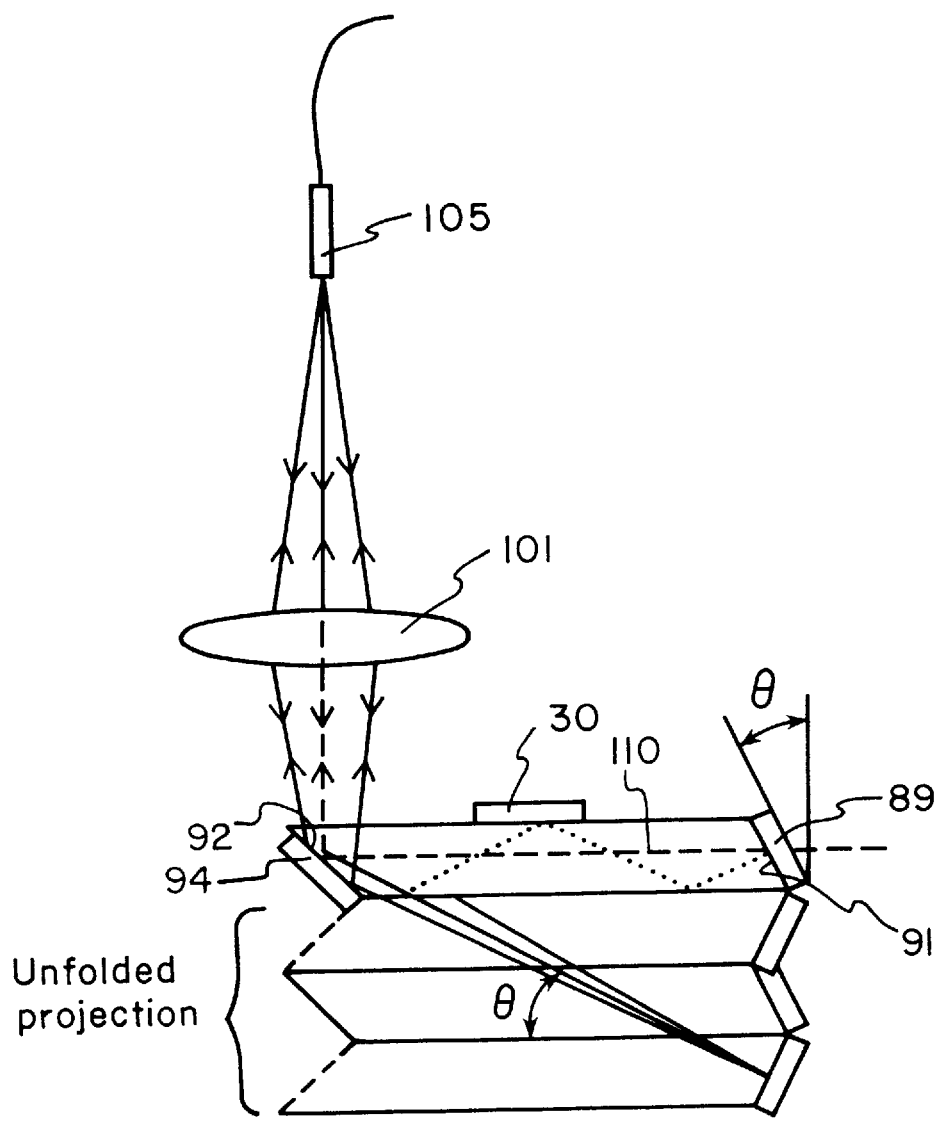
FIG. 15 is a schematic drawings not necessarily drawn to scale of another single-fiber (for both input and output) auto-collimation configurations of folded lightpipe sensors or probes. Each of these configurations is readily adapted to the probe device configuration of FIG. 12A.

FIGS. 14A, 14B and 15 are schematic drawings of single-fiber (for both input and output) auto-collimation configurations of folded lightpipe sensors or probes. Each of these configurations is readily adapted to the probe device configuration of FIG. 12A. All three illustrated configurations employ folded lightpipes with beveled, i.e., angled, longitudinal ends, input/output or distal ends. In each case, converging light is launched from an optical fiber through the illustrated input/output optics into the lightpipe, so that it fills only one band of angles. In each case, light exits the lightpipe (at the input/output end) after reflection off the sensing area and the mirror on the distal end of the lightpipe returning through the input/output optics to be focused into a single fiber pickup. The folded lightpipe configurations FIG. 14A illustrates on-axis input/output optics. In folded lightpipe 100, the input/output end face (92) is optionally beveled at angle θ to be perpendicular to the central ray of the input light band to minimize refraction at the face. This beveling is optional. The mirrored distal end face (91) is angled to be perpendicular to the central ray of the input band to direct light back out of the lightpipe and optics into the fiber. Telecentric lens (40) positioned on the optical axis of the lightpipe focuses input light from fiber 105 onto the mirrored distal face. Note that the fiber output/receiver 105 is positioned with respect to the telecentric lens (aligned with, but above the axis) to allow input light to be focused on the mirror. The focus need not be exactly on the distal end face, however, if it is focused on the mirror the system has greater angular tolerance. The illustrated focused configuration can tolerate some angular variance in the input light and still have most of the light will end up back at the fiber. If the input light were collimated through the input/output end, the system would have essentially the same light trace as that illustrated in the unfolded projection shown, but the angular tolerance of the system would be lower and small angle changes would cause the light to miss the fiber return 105.

The configuration of FIG. 14B is similar to that of FIG. 14A, but includes off-axis input/output optics. In this case, a lens (101), not a telecentric lens, is positioned to be angled up above the optic axis of the folded lightpipe. The fiber output is collinear with the lens. This configuration has the same trace as that of FIG. 14B as illustrated by the unfolded projection provided. The use of an off-axis lens allows design freedom and facilitates excitation of higher angular bands compared to the on-axis telecentric lens. The off-axis optics can also employ a telecentric lens, with appropriate repositioning of the fiber output.

The configuration of FIG. 15 is optically analogous to those of FIGS. 14A and 14B, as illustrated by the unfolded projection provided in the figure. In this case, folded lightpipe 110 is beveled at 45° at its input/output end (92) to couple light into the lightpipe by TIR and facilitate coupling out of the lightpipe. The input/output bevel is optionally mirrored (94). The lightpipe is angled (θ) at its distal mirrored end (34), as in the folded lightpipe of FIGS. 14A and B,) to be perpendicular to the central ray of the input band to direct light back out of the lightpipe and optics into the fiber. The input/output optics are on-axis (with respect to the beveled input/output face). Lens (101), which is optionally replaced with a telecentric lens, focuses input light onto the mirrored distal end face. These single fiber configurations can be readily adapted to have multiple sensing channels across the width of the lightpipe.

Figure 16A:
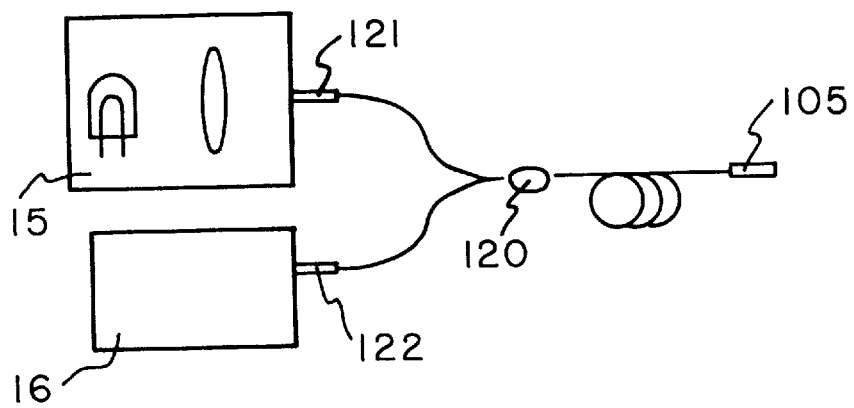
FIGS. 16A–C illustrate three alternative fiber optic coupler systems not necessarily drawn to scale for use with probes and sensors of this invention.
Figure 16B:
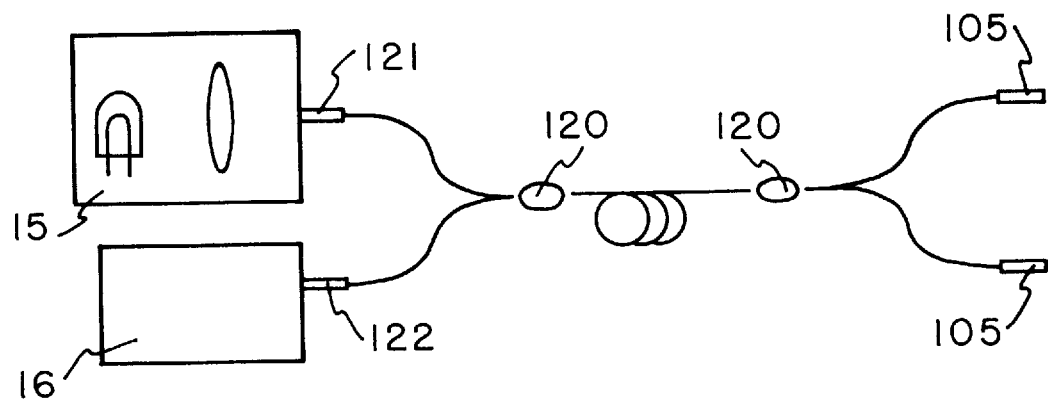
Figure 16C:
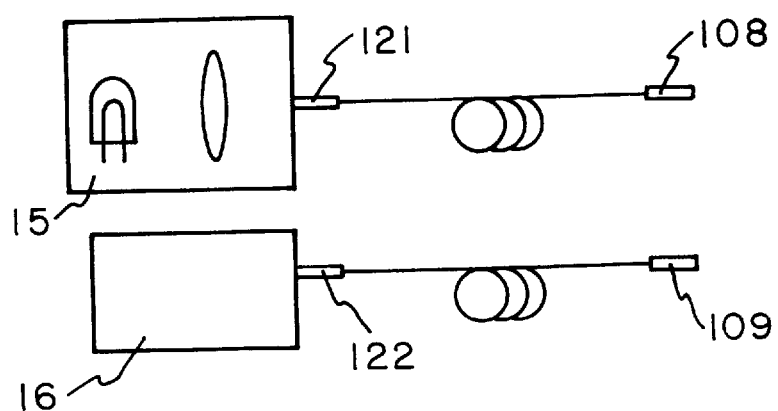

FIG. 16 illustrates three alternative fiber optic coupler systems for use with probes and sensors of this invention. The coupling system of FIG. 16A is particularly useful with the single-fiber configurations disclosed herein. Fiber coupler 105 is optically coupled to both a light source and a detector via a fiber beam splitter 120. The coupling system of FIG. 16B provides for interface with two fiber configurations via fiber beam splitter 120, for example, separate input and output fibers such as can be employed in the probe of FIG. 12A. Alternatively, this system can be employed to interface two single-fiber probe configurations to a light source and detector. Finally, the coupling system of FIG. 16C provides separate fiber couples 108 and 109 for input from the light source and output to a detector respectively.

Those of ordinary skill in the art know how to select appropriate fiber optic coupling systems and fiber optic components for light input and output from configurations such as those described herein.

Printz, M. et al. (1993) *J. Modern Optics* 40 (11):2095–2104 and Bussiager, R. and Macloud, H. (1995) *J. Modern Optics* 42(7):1355–1360 have described a variation of SPR that is designated "inverted SPR". These references are incorporated by reference herein for their description of "inverted SPR." This method differs from traditional SPR in that the SPR-sensing layer comprises a thicker layer (about 100 Å) of a metal, like chromium, which is usually used in an adherence layer, with a thinner layer of gold or silver (about 400 Å) on top (i.e., for contact with dielectric samples). The SPR signal has an inverted feature in it and the wavelength of the resonance for a given sample is shifted from that measured by SPR. The sensor configurations of this invention can be employed for inverted SPR by appropriate adjustment of the layers of the sensing areas.

The description of SPR provided herein above relates to interaction of light at the interface of 3-layer smooth surfaces. SPR is known to occur at 2-layer rough surfaces. The SPR sensor configurations of this invention can be readily adapted for use with such alternative SPR mechanisms by appropriate modification of the SPR sensing area.

A variety of monochromatic and non-monochromatic sources of incident radiation are readily available. Monochromatic sources include laser sources, e.g., diode lasers, and gas discharge sources. In addition, a monochromatic source can be generated by coupling of white light or other multiple wavelength source with a wavelength selective filter or with a monochromator. Non-monochromatic sources include combinations of two or more monochromatic sources including, one or more LED's, arc sources, black body sources, and certain gas discharge sources, e.g., neon indicator lamps. A tungsten halogen lamp, for example, is a suitable white light source. Best results are obtained when the current in, and temperature of, the white light source are controlled in order to minimize any background spectral variation. Conventional fiber optics systems (configured with appropriate splitters and couplers) can be used to convey light from a remote source to a sensor or probe and/or from the output optics of the sensor to a remote detector. Alternatively, the source, detector or both can be directly associated (i.e., not remote from) with the sensor or probe.

A variety of detector schemes applicable to analysis of the output light of the sensors of this invention are known and readily available to those in the art, including spectrographs, fixed linear array detectors, CCDs (charge coupled devices), photodiode arrays, monochromators, mechanically tunable wavelength output and a single detector, electronically tunable filters (scanning etalon), dispersing prisms and wedge etalons. For example, a photodetector can be combined with a series of bandpass filters, e.g., a filter wheel. Passage of the light exiting the lightpipe through a filter wheel allows selection by rotation of the wheel of a narrow bandpass of the light for wavelength-selective intensity measurement with the photodetector. Detection systems can alternatively employ a dispersing prism, linear variable interference filters or individual interference filters when only a limited number of wavelengths are of interest.

U.S. Pat. No. 5,374,563 describes SPR sensors that employ phase modulation detection. Nelson, S. G. et al. (1996) "High Selectivity Surface Plasmon Resonance Sensor Based on Phase Detection" presented at the Sixth International Conference on Chemical Sensors (Jul. 22–24, 1996) Washington, D.C. also described SPR sensor configurations that employ phase modulation detection. One particular difference in the use of phase modulation is that the input light comprises TM and TE polarized light. The SPR sensors of this invention can be modified or adapted in view of these references and what is known in the art about SPR and phase modulation to employ phase modulation detection, particular those methods specifically described in the cited references.

The output optics of the folded lightpipes of this invention preferably include a means for correcting for spherical and chromatic aberrations so that a good image of the source corresponding to each angular band can be formed. This type of correction can be accomplished for example using a field flattener.

Since it is possible to calculate the precise range of angles in each band of light (exiting the lightpipe or propagating through the lightpipe), the lightpipe sensor of FIG. 3A in which the sensing area consists of an SPR-supporting conductor layer, specifically an SPR-supporting metal layer, of known thickness can be calibrated using a model matching technique. By measuring the length and thickness of the lightpipe with a micrometer, the angles of each band can be calculated with high precision. If the thickness of the metal sensing layer is accurately known, a Fresnel reflection model can be used to find the RI which would excite SPR at the measured resonance angle. If the metal thickness measurement is not accurate, metal thickness in the model can be corrected by using a liquid standard whose RI is measured on an Abbe refractometer or by other appropriate methods. Metal thickness can be adjusted in the model until the modeled resonance at the wavelength at which the standard is measured matches the experimental resonance of the liquid standard.

An anamorphic lens beam expander, which is a lens system that magnifies a beam of light in only one direction, can be employed optionally in combination with other optical components in the input or output optics of the SPR sensors of this invention. These lens systems are particularly useful for input into lightpipe sensors having a plurality of sensing areas across the width of the lightpipe.

In general, lens and related components employed to collimate or focus light into the SPR sensor configurations or out of the sensor of this invention are preferably achromatic.

The range of RI that can be measured with a given sensor depends upon incident angle, substrate RI, wavelengths of illumination/detection, choice of sensing metal, dynamic range controlling layer and to some extent the metal thickness. RI values above $n_{glass}$ can only be detected when using a dynamic range controlling layer.

The term "substantially" has been used to modify several absolute terms herein, e.g., substantially single angle, substantially collimated, substantially parallel and substantially monochromatic. The term is used to indicate that some deviation from the absolute is tolerated in the configurations described herein. In some cases, for example, in "substantially collimated", the term indicates that it is not, in a practical sense, possible to achieve absolute, i.e., perfectly collimated light. This is appreciated and understood by those in the art. Thus, in the "single angle" configurations of this invention imperfections in collimation of input light will lead to a small range of incidence angles at the sensing area and the configuration will only be substantially single angle.

The term "analyte" is used herein generically to refer to any chemical or biological molecule (nucleic acid, antibody, antigen, blood factor or component, etc.) that is to be detected. The devices and methods of this invention can be used for the quantitative or qualitative detection of one or more analytes in gas or liquid samples. The device and methods of this invention can be employed in the analysis of a solid sample or of a thin film in contact with the sensing area.

The sensors and probes of this invention can be employed in a variety of applications. In general, they can be employed in any application which currently employs a prism or waveguide SPR sensor configuration. These sensors can be adapted as discussed above for use in biological sensing applications, e.g., as biosensor, or use in flow or static sample systems. They will be particularly useful in low cost applications, such as hand-held SPR instrumentation. Specific examples of applications include use as a detector in instrumental effluent stream, such as in HPLC methods or for the detection of corrosion of metals.

The SPR sensors and probes of this invention are useful in industrial process control applications, such as environmental waste stream monitoring, in pharmaceutical production and in food and beverage production.

The sensors of this invention can be employed in combination with other analytical methods including, for example, electrochemical methods. In particular, the sensors of this method can be employed in the combined electrochemical and SPR methods that have been described, for example in methods described in U.S. Pat. No. 4,889,427; in Gordon, J. G and Ernst, S. (1980) Surface Science 101:499–506 and in U.S. provisional patent application Ser. No. 60/007,026, filed Oct. 25, 1995 and corresponding U.S. patent application (Attorney Docket No. 90–95) filed Oct. 25, 1996, all of which are incorporated by reference herein for their disclosure of combined electrochemical and SPR methods.

U.S. Pat. No. 5,485,277 discloses the use of SPR sensors for enhanced fluorescence measurements. The methods disclosed combine a fluorescence detector positioned with respect to the SPR metal layer to detect fluorescence from the layer. SPR sensors of this invention can be readily adapted with appropriate fluorescence detectors for use in such methods.

U.S. Pat. No. 5,313,264 describes the use of an optical multi-analyte sensor system based on internal reflection of polarized light in combination with detection methods based on the evanescent wave phenomenon at TIR including SPR, critical angle refractometry, TIR fluorescence, TIR phosphorescence, TIR light scattering and evanescent wave ellipsometry. The SPR sensors of this invention can be readily adapted or modified in view of the disclosures herein, in U.S. Pat. No. 5,313,264 and in view of methods, techniques and devices that are well-known in the art, for use in combination with TIR-based detection systems, particularly those mentioned above.

EXAMPLE

Example 1

A completely adjustable sensor based having the configuration illustrated in FIG. 8 was constructed. The probe is 20 mm in diameter by a total of 100 mm long and capable of picking up two output bands simultaneously. Fiber optic cables were used to introduce broad band white light and return the output light to a spectrograph detector. The folded planar lightpipe sensor element was made from a 5 mm ×16 mm ×1 mm (W×L×t)piece of float glass (a microscope slide cut to the desired size) which was polished on both longitudinal ends. A gold mirror was deposited on one end of the folded lightpipe and a 52.5 nm (525 Å) gold sensing layer was deposited on the top planar surface of the lightpipe covering the last 10 mm (extending about 63% of the total length) of the lightpipe toward the distal mirrored end.

Figure 17A:
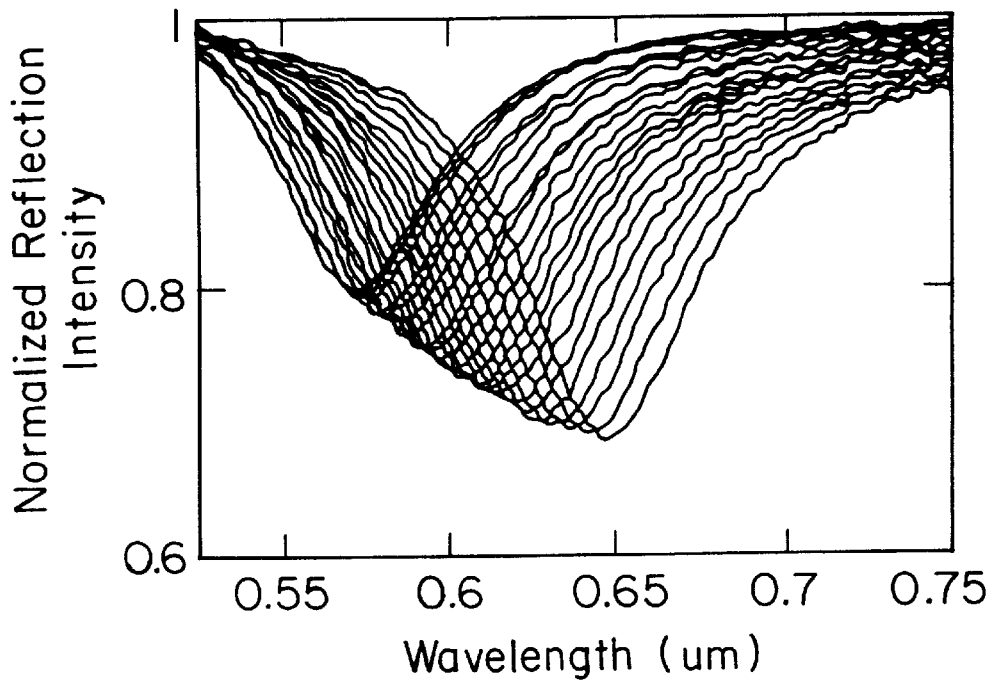
FIG. 17A is a graph of normalized reflection spectra of aqueous glucose solutions of known concentration measured with the lightpipe probe of this invention as described in Example 1.
Figure 17B:
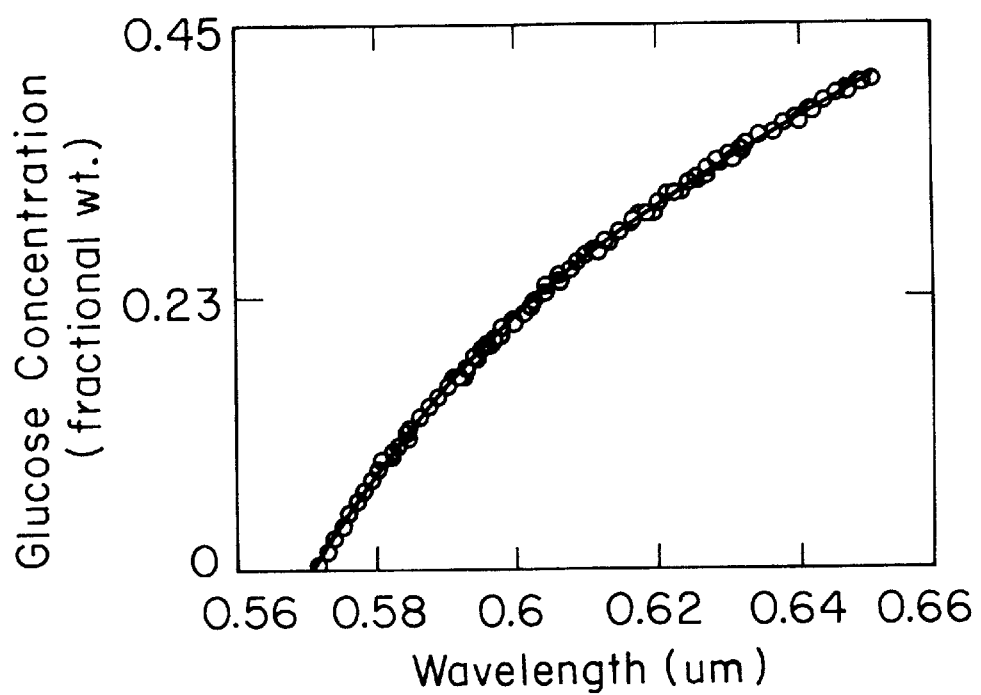
FIG. 17B is a calibration plot of glucose concentration vs. $\lambda_{SPR}$ based on the data of FIG. 17A.

The SPR response for angular band 6 exiting from the lightpipe was examined. Measurements of 75 samples of aqueous glucose solutions of known concentration ranging from 0% to 41% by weight of solution were made with the probe sensor. FIG. 17A shows a sampling of the reflection spectra of aqueous glucose acquired. The shallow depth of the resonances is believed to be partially due to TE light in the system and partially due to the sensing film being too thick. FIG. 17B shows the calibration plot of glucose concentration vs. $\lambda_{SPR}$. Due to the noise in the system, there was some uncertainty in $\lambda_{SPR}$ and the RI sensitivity of this probe configuration was found to vary between $1.4\times10^{-4}$ and $2.8\times10^{-5}$ IRU (Index of Refraction Units).

Those of ordinary skill in the art will appreciate that methods, materials and techniques other than those specifically discussed herein can be readily employed or adapted to implement the sensor configurations and practice the methods of this invention. For example, a variety of means for measuring reflection coefficients and/or light intensity, particular as a function of wavelength, are well-known and available to those in the art. In addition, there are a variety of techniques and devices known for collimating, collecting, expanding, magnifying, focusing and conducting light that can be applied or readily adapted to light input to or light output from the sensors of this invention. Those of ordinary skill in the art can readily select from among such alternatives, variants and functional equivalents those that are appropriate for use in the SPR configuration of this invention.

All of the references cited in this specification are incorporated by reference in their entireties herein.

We claim:

1. A surface plasmon resonance sensor which comprises:
   a planar lightpipe having two longitudinal ends: an input/output end and a distal end, a sensing area on an external planar surface of said lightpipe said sensing area comprising a conducting layer that supports surface plasmon resonance, and a mirror at said distal end of the lightpipe;

a light source optically coupled to the input/output end of said lightpipe to introduce light into said lightpipe such that the light is conducted through said lightpipe by total internal reflection to reflect off the mirror at said distal end to be conducted back through said lightpipe by total internal reflection to exit the lightpipe at said input/output end in angular bands wherein during said double pass through said lightpipe, the light reflects off said sensing area exciting a surface plasmon wave therein; and a detector for receiving angular bands of light exciting said input/output end of said lightpipe and reflected off said sensing area which thereby detects surface plasmon resonance excited by said light incident upon said sensing area.

2. The sensor of claim 1 wherein said light source is a multiple wavelength light source.

3. The sensor of claim 1 wherein light is introduced into said lightpipe by focusing light from said light source at the face of the input/output end of said lightpipe.

4. The sensor of claim 1 wherein said light is introduced asymmetrically at a range of angles filling angles on only one side of the optical axis of the lightpipe.

5. The sensor of claim 1 wherein said light is introduced into said lightpipe at a range of angles filling angles on either side of the optical axis of the lightpipe.

6. The sensor of claim 1 wherein said lightpipe comprises two or more sensing areas on an external planar surface.

7. The sensor of claim 6 wherein one of said sensing areas is a reference sensing area.

8. The sensor of claim 6 wherein said lightpipe comprises a plurality of sensing areas across the width of the lightpipe.

9. The sensor of claim 6 wherein said lightpipe comprises a plurality of sensing areas along the length of the lightpipe.

10. The sensor of claim 1 wherein said sensing area comprises a SPR-supporting metal layer.

11. The sensor of claim 10 wherein said sensing area comprises an adherence layer.

12. The sensor of claim 10 wherein said sensing area comprises a reactive layer.

13. The sensor of claim 12 comprising a plurality of sensing areas along the width of the lightpipe and wherein at least one of said sensing areas is a reference sensing area.

14. The sensor of claim 13 wherein said sensing areas that are not reference sensing areas each comprise a reactive layer.

15. The sensor of claim 14 wherein, in each of said sensing areas that comprises a reactive layer, the reactive layer is specific for a different analyte.

16. The sensor of claim 10 wherein said sensing area comprises a dynamic range-controlling layer.

17. The sensor of claim 1 wherein the detector is a spectrograph.

18. The sensor of claim 1 wherein the detector is a CCD camera.

19. The sensor of claim 1 wherein the detector comprises a fiber optic pickup.

20. The sensor of claim 1 which comprises a telecentric lens optically coupled to said input/output end of said lightpipe.

21. The sensor of claim 20 wherein said telecentric lens is a spherical telecentric lens.

22. The sensor of claim 20 wherein said telecentric lens is a cylindrical telecentric lens.

23. The sensor of claim 22 wherein said telecentric lens functions both for light input into and collection of angular bands of light exiting said lightpipe.

24. The sensor of claim 23 farther comprising a spherical collimator optically coupled to said light source for receiving and collimating light from said source and also optically coupled to said telecentric lens such that collimated light from said spherical collimator is focused by passage through said telecentric lens at the face of the input/output end of said lightpipe.

25. The sensor of claim 1 wherein a sensing area is positioned on an external planar surface of said lightpipe within an area beginning at the distal end of the lightpipe and extending up to about 75% of the total length of the lightpipe from the distal end of the lightpipe.

26. The sensor of claim 25 wherein the sensing area is curved along its width to minimize multiple reflections off of the sensing area.

27. The sensor of claim 26 wherein the mirror at the distal end of said lightpipe is curved to have a constant radius that is equal to the length of the lightpipe.

28. The sensor of claim 26 wherein the mirror at the distal end of said lightpipe is curved to have a constant radius that is equal to twice the length of the lightpipe.

29. The sensor of claim 1 wherein the mirror at the distal end of said lightpipe is curved to have a constant radius that is equal to the length of the lightpipe.

30. The sensor of claim 29 further comprising a spherical telecentric lens optically coupled to said light source to focus light from said source at the face of the input/output end of said lightpipe and to receive output light from said lightpipe.

31. The sensor of claim 30 further comprising a collimating lens optically coupled between said light source and said telecentric lens and an imaging lens optically coupled between said telecentric lens and said detector to receive and focus output light at said detector.

32. The sensor of claim 1 wherein the face of the input/output end of said lightpipe is beveled and light is introduced into said lightpipe by focusing on said beveled end face.

33. The sensor of claim 32 wherein the beveled input/output end face of said lightpipe is mirrored.

34. The sensor of claim 33 wherein light is introduced into said lightpipe by reflection off said mirrored bevel on said input/output end face.

35. The sensor of claim 34 further comprising a telecentric lens optically coupled to said lightpipe for simultaneously focusing light from said source into said lightpipe and collecting angular output bands from said lightpipe and focusing them to said detector.

36. The sensor of claim 35 wherein said sample cell is a flow cell.

37. The sensor of claim 1 further comprising a sample cell adjacent to said lightpipe sensor which allows a gas or liquid sample to interface with a sensing area of the lightpipe.

38. The sensor of claim 1 further comprising a TM polarizer optically coupled anywhere within said sensor to exclude TE polarized light from said detector.

39. The sensor of claim 1 wherein said lightpipe is fabricated from glass or crystal.

40. The sensor of claim 39 wherein said lightpipe is substantially coated with a cladding layer having an index of refraction lower than that of the lightpipe substrate, except that the cladding does not cover said sensing area.

41. The sensor of claim 1 wherein said lightpipe is fabricated from plastic or a polymer material.

42. The sensor of claim 41 wherein said lightpipe is substantially coated with a cladding layer having an index of refraction lower than that of the lightpipe substrate except that the cladding does not cover the sensing area.

43. The sensor of claim 1 which comprises a fiber optic coupler which functions both to conduct light from said light source to said lightpipe and to carry light exiting said lightpipe to said detector.

44. The sensor of claim 43 further comprising a telecentric lens optically coupled between said fiber optic coupler and said lightpipe which functions both to focus input light at the mirror of said distal end of said lightpipe and to focus light exiting said lightpipe into said fiber optic coupler.

45. The sensor of claim 1 wherein both ends of said lightpipe are beveled at the same angle and input light is coupled into the lightpipe by focusing at the beveled mirror of the distal end of the lightpipe.

46. An method for surface plasmon resonance measurement of a sample which comprises the steps of contacting the sample with a sensing area of an surface plasmon resonance lightpipe sensor of claim 1 and detecting the reflection spectrum of angular bands of light exiting said lightpipe.

* * * * *

UNITED STATES PATENT AND TRADEMARK OFFICE
CERTIFICATE OF CORRECTION

PATENT NO. : 5,815,278

DATED : September 29, 1998

INVENTOR(S) : Johnston et al.

It is certified that error appears in the above-identified patent and that said Letters Patent is hereby corrected as shown below:

<u>In the claims:</u>

In claim 37, line 2, delete "said lightpipe sensor" and replace with --a sensing area of said lightpipe--.

In claim 46, line 1, change "An" to --A-- and in line 2, delete "which".

In column 4, line 3, delete "ultimate" and replace with --ultimately--.

In column 5, line 11, delete "or both".

In column 6, line 7, delete "lightpipe" and replace with --lightpipes--.

In column 7, line 5, delete "11$b$" and replace with --11B--.

In column 7, line 23, delete "drawings" and replace with --drawing--.

In column 9, line 13, delete the second parenthesis following "$\lambda$".

In column 10, line 66, delete "surface," and replace with --surfaces,--.

UNITED STATES PATENT AND TRADEMARK OFFICE
CERTIFICATE OF CORRECTION

PATENT NO. : 5,815,278

DATED : September 29, 1998

INVENTOR(S) : Johnston et al.

It is certified that error appears in the above-identified patent and that said Letters Patent is hereby corrected as shown below:

In column 11, line 11, delete "carry" and replace with --carrying--.

In column 11, line 30, delete "angle" and replace with --angles--.

In column 12, line 17, delete "a" preceding "graphs".

In column 12, line 24, delete "This" and replace with --These--.

In column 13, line 18, delete "entering" and replace with --enters--.

In column 14, line 57, delete "locating" and replace with --location of--.

In column 15, line 11, delete "provide" and replace with --provided--.

In column 17, line 51, delete "is".

In column 19, line 27, delete "For" and replace with --for--.

In column 19, line 63, insert --can-- between "and" and "be".

In column 19, line 66, delete "11*b*" and replace with --11B--.

In column 20, line 19, delete "absorption" and replace with --adsorption--.

UNITED STATES PATENT AND TRADEMARK OFFICE
CERTIFICATE OF CORRECTION

PATENT NO. : 5,815,278

DATED : September 29, 1998

INVENTOR(S) : Johnston et al.

It is certified that error appears in the above-identified patent and that said Letters Patent is hereby corrected as shown below:

In column 21, line 65, insert --lightpipe-- before "sensor" and --90-- following "sensor".

In column 22, line 9, delete "with in" and replace with --within--.

In column 22, line 31, delete "configurations" and replace with --configuration--.

In column 22, line 48, delete "will".

In column 23, line 7, delete the parenthesis following "B,".

In column 23, line 28, insert a comma following "detector".

In column 23, line 62, delete the comma following "including".

In column 26, lines 50 and 51, delete "particular" and replace with --particularly--.

Signed and Sealed this

Twelfth Day of January, 1999

Attest:

Attesting Officer

*Acting Commissioner of Patents and Trademarks*